(12) United States Patent
Srinivasan

(10) Patent No.: US 8,999,937 B2
(45) Date of Patent: Apr. 7, 2015

(54) GLUCOCORTICOID INDUCED LEUCINE ZIPPER MIMETICS AS THERAPEUTIC AGENTS IN MULTIPLE SCLEROSIS

(75) Inventor: Mythily Srinivasan, Greenwood, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 14/001,716

(22) PCT Filed: Feb. 28, 2012

(86) PCT No.: PCT/US2012/026962
§ 371 (c)(1),
(2), (4) Date: Aug. 27, 2013

(87) PCT Pub. No.: WO2012/118821
PCT Pub. Date: Sep. 7, 2012

(65) Prior Publication Data
US 2013/0338077 A1    Dec. 19, 2013

Related U.S. Application Data

(60) Provisional application No. 61/447,436, filed on Feb. 28, 2011.

(51) Int. Cl.
| | |
|---|---|
| *C07K 14/47* | (2006.01) |
| *A61K 38/07* | (2006.01) |
| *A61K 38/08* | (2006.01) |
| *A61K 38/10* | (2006.01) |
| *A61K 38/16* | (2006.01) |

(52) U.S. Cl.
CPC .............. *C07K 14/4713* (2013.01); *A61K 38/07* (2013.01); *A61K 38/08* (2013.01); *A61K 38/10* (2013.01); *A61K 38/16* (2013.01)

(58) Field of Classification Search
CPC ....... A61K 38/07; A61K 38/08; A61K 38/10; C07K 14/4713
See application file for complete search history.

(56) References Cited

U.S. PATENT DOCUMENTS

| | | |
|---|---|---|
| 2004/0194160 A1 | 9/2004 | Riccardi |
| 2009/0061462 A1 | 3/2009 | Michelitsch et al. |
| 2010/0055701 A1 | 3/2010 | Tong et al. |

FOREIGN PATENT DOCUMENTS

| | | | | |
|---|---|---|---|---|
| WO | WO 2007/045247 | * | 4/2007 | ............. C07K 14/47 |

OTHER PUBLICATIONS

PCT International Search Report and Written Opinion completed by the ISA/US on Jul. 31, 2012 and issued in connection with PCT/US2012/026962.

Ayroldi, et al. "Glucocorticoid-Induced Leucine Zipper (GILZ); a New Important Mediator of Glucocorticoid Action" The FASEB Journal (2009), vol. 23, p. 3649-3658; p. 3654, col. 1, paragraph 2, Fig. 1.

* cited by examiner

*Primary Examiner* — John Ulm
(74) *Attorney, Agent, or Firm* — Barnes & Thornburg LLP

(57) ABSTRACT

Polypeptide compositions that mimic the activity of glucocorticoid induced leucine zipper (GILZ) on the immune system are described. Also described is a method of treating multiple sclerosis using compositions comprising GILZ or lower molecular weight polypeptides with structural relationships to GILZ.

10 Claims, 23 Drawing Sheets

GLUCOCORTICOID INDUCED LEUCINE ZIPPER MIMETICS AS THERAPEUTIC AGENTS IN MULTIPLE SCLEROSIS

CROSS REFERENCE TO RELATED APPLICATIONS

This application is a U.S. national counterpart application of International Application No. PCT/US2012/026962 filed Feb. 28, 2012, which claims priority to U.S. Provisional Patent Application No. 61/447,436 filed Feb. 28, 2011. The entire disclosures of PCT/US2012/026962 and USSN 61/447,436 are hereby incorporated by reference.

INCORPORATION BY REFERENCE OF MATERIAL SUBMITTED ELECTRONICALLY

Incorporated by reference in its entirety is a computer-readable amino acid sequence listing submitted concurrently herewith and identified as follows: One 4 KB ACII (Text) file named "220511_ST25.txt" created on Aug. 13, 2013.

TECHNICAL FIELD

The invention pertains generally to compositions that mimic the activity of glucocorticoid induced leucine zipper (GILZ) on the immune system. More particularly, the invention pertains to the use of GILZ mimetics for treatment of multiple sclerosis.

BACKGROUND AND SUMMARY

Glucocorticoids act by interacting with the glucocorticoid receptor (GR) in the cytoplasm, which then translocates to the nucleus and binds the GR responsive elements (GRE) in the promoter regions of target genes. Glucocorticoid induced leucine zipper (GILZ) (SEQ ID NO: 1) is a glucocorticoid-inducible gene with six GRE elements. Overexpression of GILZ suppresses activated T cells by inhibiting transactivation of nuclear factor kappa B (NF-κB), the master regulator of inflammatory responses. The anti-inflammatory activity of synthetic glucocorticoids mediated by preventing NF-κB transactivation has been attributed to the induced upregulation of GILZ (SEQ ID NO: 1).

Multiple sclerosis (MS) is a common chronic inflammatory and demyelinating disease of the central nervous system. MS affects young and middle aged adults, and women in particular, imposing significant economic costs on individuals and the community in terms of loss of productivity and efficiency. MS is widely recognized as a complex disease driven by dysregulated immunity accompanied by relapsing and remitting clinical manifestations. There are many symptoms associated with MS, including weakness, fatigue, sensory loss, paresthesias, optic neuritis, diplopia, ataxia, vertigo, pain, lhermitte, demenital, visual loss, and inflammation. The pivotal role played by NF-κB in the pathogenesis of MS is well established. Peptides derived from the NF-κB essential modulator (NEMO), the NEMO binding unit (NBD) of IKKβ proteins and the phosphorylation sites of p65 have been evaluated to directly target the NF-κB multisubunit complex.

The ability of currently available therapeutic agents to modify the disease course in MS is modest at best. Hence, there is a need for developing more effective disease-modifying therapies. MS is widely recognized as a complex disease driven by dysregulated immunity accompanied by relapsing and remitting clinical manifestations. Since the antigenic trigger of MS is not definitively identified, most disease modifying agents are designed to modulate the inflammatory response in the periphery and in the brain. Therapies under development include strategies that deplete lymphocytes and those that mediate immunomodulation. Since depletion could potentially cause global immunosuppression, strategies of immunomodulation are preferable.

The profound anti-inflammatory activity of synthetic glucocorticoids, combined with their ability to induce lymphocyte apoptosis place them among the most commonly prescribed drugs in the management of relapse in MS. However, poor efficacy in reducing the frequency or severity of relapse and the complications of serious side-effects compromise the continuous or long-term use of steroids. Hence, treatments that harness the therapeutic effects of glucocorticoids with a better benefit-to-risk ratio than traditional steroids are needed.

GILZ, originally identified as a glucocorticoid-inducible gene, has been shown to interact with the p65 subunit of NF-κB in activated T cells. Since activated p65 is present only in stimulated cells, the GILZ mimetics may mediate selective inhibition of activated cells without causing widespread immunosuppression. Preliminary results suggest that treatment with exogenous GILZ (SEQ ID NO: 1) suppresses antigen activated T cell responses in vitro. Low molecular weight GILZ mimetics that bind the p65 protein with optimal kinetics are characterized. Advantages of peptides such as GILZ mimetics as therapeutics include non-immunogenicity with potential for long-term use, greater permeability to cross tissue barriers, and cost-effectiveness.

One of the actions of glucocorticoids is to modulate the transcription of multiple genes involved in immune response. The anti-inflammatory effect is largely attributed to the inhibition of nuclear factor kappa B (NF-κB), a regulator of inflammatory responses. GILZ having an amino acid sequence MNTEMYQTPMEVAVYQLHNFSISFFSSLLGGDVVSVKLDNSASGASVVAIDNKIEQAM DLVKNHLMYAVREEVEILKEQIRELVEKNSQLERENTLLKTLASPEQLEKFQSCLSPEEP AP ESPQVPEAPGGSAV (SEQ ID NO: 1), is a glucocorticoid induced gene that binds the p65 subunit of NF-κB to inhibit its nuclear translocation.

NF-κB is a heterodimer of p50 and p65 that remains as an inactive complex with inhibitory proteins such as IκB in the cytoplasm of resting T cells. Following T cell activation, p65 is released from the inhibitory complex, translocates to the nucleus and mediates transactivation of inflammatory genes. Gene profiling studies revealed the presence of elevated p65 in the peripheral blood monocytes and in the pathologic lesions in MS. It is believed herein that therapeutic agents that sequester activated p65 within the cytoplasm will suppress transactivation of inflammatory cytokines and ameliorate disease in MS. Based on analysis of mutational and functional studies, it is believed herein that the proline rich carboxy terminus of GILZ (SEQ ID NO: 1) interacts physically with the p65 subunit of NF-κB. Proline rich regions (PRR) are often localized in the solvent exposed regions of proteins involved in transient interactions such as signaling or cytoskeletal rearrangements. Hence PRRs provide target sites for developing inhibitors of transient protein-protein interactions. Rationally designed peptide mimetics of the proline rich p65 binding interface of GILZ (SEQ ID NO: 1) may sequester p65 within the cytoplasm in activated T cells and suppress inflammation related to MS. Without being bound by any particular theory, such peptide mimetics may act as a glucocorticoid mimetic and/or as an NF-κB inhibitor.

Knowledge derived from the primary structure of GILZ (SEQ ID NO: 1) and its interaction with the p65 subunit of NF-κB is applied to the design of novel peptide agents, the GILZ mimetics. The carboxy terminus of GILZ (GILZ-COOH) consists of 35 residues (residues 100-134 of GILZ); LASPEQLEKFQSCLSPEEPAPESPQVPEAPGGSAV (SEQ ID NO: 2). Significantly, it has three "PXXP" motifs: PEEP (SEQ ID NO: 3), PESP (SEQ ID NO: 4), and PEAP (SEQ ID NO: 5). The structural and functional significance of this motif in transient intermolecular interactions such as cytoskeletal rearrangement and signaling is well established. Secondary structure prediction of GILZ-COOH by the nearest neighboring neural network suggested a helical conformation between 103P-S111 indicating a region with significant propensity to bind DNA. Hence, synthetic peptides corresponding to one or more proline rich regions of GILZ may be effective GILZ mimetics.

Localized in the solvent exposed domains, the role of PRRs is to bring proteins together so as to make subsequent interactions more probable. This is particularly true for interactions between functionally important proline and conserved hydrophobic residues in the interface of its binding partner. Notably, the transactivation domain of p65 that potentially interacts with the GILZ protein presents two highly conserved phenylalanine residues; F534 and F542 which together with the conserved acidic residues at $Asp^{531}$ and $Asp^{533}$ and phosphorylation sites at $Ser^{529}$ and $Ser^{536}$ constitute the critical residues for p65 transactivation. Data from these observations are integrated with that from residue interface propensity to introduce rational amino acid substitutions and/or truncations in the GILZ-WT so as to design GILZ mimetics with optimal p65 binding efficacy. Additional parameters considered to increase the drug like properties of GILZ mimetics include solvent mediated contact potential, accessible surface volume/residue, log interface residue propensity, weighted hydrophobicity and solvation potential.

Conventionally, the proof of therapeutic manipulation of specific intermolecular interactions is derived from studies using fusion proteins and/or monoclonal antibodies of the interacting molecules such as Abatacept (CTLA4 IgG1Fc), Alefacept (LFA-3-IgG1Fc), Denileukin diftitox (recombinant IL-2) and Etanercept (TNFR-IgG1Fc) or adalimumab/Certolizumab pegol/infliximab (anti-TNF-α mAb), Natalizumab (anti-α4 integrin,) and Efalizumab (anti-CD11a mAb) respectively. These agents target interactions occurring at cell surface and/or in the extracellular environment. In contrast, the GILZ:p65 interaction occurs in the cytoplasm necessitating intracellular delivery of potential modulating agent(s). In this context, low molecular weight peptides that are permeable and better amenable for intracellular delivery than large proteins represent attractive alternatives.

Without being bound by any particular theory, it is believed that because activated p65 is present only in activated T cells, intracellular delivery of GILZ mimetics will suppress pro-inflammatory responses by sequestering activated p65 and facilitate skewing towards anti-inflammatory responses. An advantage of lower molecular weight peptides as therapeutic agents include increased permeability for intracellular delivery compared to larger proteins.

The following numbered embodiments are contemplated and are non-limiting:

1. A pharmaceutical composition comprising a polypeptide from about 6 to about 35 amino acid residues, the polypeptide comprising 1 to 3 tetrapeptides having the sequence of PXXP, wherein
   P is proline; and
   X is any amino acid.

2. The pharmaceutical composition of clause 1, wherein at least one tetrapeptide comprises the amino acid sequence of SEQ ID NO: 3.

3. The pharmaceutical composition of clause 1 or clause 2, wherein at least one tetrapeptide comprises the amino acid sequence of SEQ ID NO: 4.

4. The pharmaceutical composition of any one of clauses 1 to 3, wherein at least one tetrapeptide comprises the amino acid sequence of SEQ ID NO: 5.

5. The pharmaceutical composition of clause 1, wherein the polypeptide comprises the amino acid sequence of CLSPEEPAPESPQVPEAPGGSAV (SEQ ID NO: 6).

6. The pharmaceutical composition of any one of clauses 1 to 5, wherein the polypeptide comprises a polyproline helical conformation.

7. The pharmaceutical composition of any one of clauses 1 to 6 further comprising a cell penetrating peptide.

8. The pharmaceutical composition of clause 7, wherein the cell penetrating peptide is selected from the group consisting of Penetratin, Pep-1, Pep-2, VP22, pVEC, pISL, hCT derived peptide, LL-37, Mouse PrP, Transportan, TP10, Arg11, MAP, MPG, KALA, ppTG1, and ppTG20.

9. The pharmaceutical composition of clause 7, wherein the cell penetrating peptide is a bipartite peptide (K16ApoE) consisting of a polylysine segment linked with the apolipoprotein-E peptide.

10. The pharmaceutical composition of clause 7, wherein the cell penetrating peptide is Pep-1.

11. The pharmaceutical composition of any one of clauses 1 to 10, wherein the composition suppresses p65 binding.

12. The pharmaceutical composition of any one of clauses 1 to 11, wherein the composition suppresses p65 activation.

13. The pharmaceutical composition of any one of clauses 1 to 12, wherein the composition inhibits NF-κB translocation to the nucleus of a cell.

14. The pharmaceutical composition of any one of clauses 1 to 13, wherein the composition suppresses T cell response.

15. The pharmaceutical composition of any one of clauses 1 to 14, wherein the composition suppresses T-bet transcription.

16. The pharmaceutical composition of any one of clauses 1 to 15, wherein the composition suppresses a pro-inflammatory cytokine.

17. The pharmaceutical composition of any one of clauses 1 to 16, wherein the composition suppresses a cytokine associated with Th-1 response.

18. The pharmaceutical composition of clause 17, wherein the cytokine is selected from the group consisting of IL-12, IL-17, IFN-γ, TNF-α, and IL-23.

19. The pharmaceutical composition of clause 17, wherein the cytokine is IL-12.

20. The pharmaceutical composition of clause 17, wherein the cytokine is IL-17.

21. The pharmaceutical composition of clause 17, wherein the cytokine is IFN-γ.

22. The pharmaceutical composition of clause 17, wherein the cytokine is TNF-α.

23. The pharmaceutical composition of clause 17, wherein the cytokine is IL-23.

24. The pharmaceutical composition of any one of clauses 1 to 23, wherein the composition enhances a cytokine associated with Th-2 response.

25. The pharmaceutical composition of clause 24, wherein the cytokine is selected from the group consisting of IL-4, IL-10 and TGF-β.

26. The pharmaceutical composition of clause 24, wherein the cytokine is IL-4.

27. The pharmaceutical composition of clause 24, wherein the cytokine is IL-10.

28. The pharmaceutical composition of clause 24, wherein the cytokine is TGF-β.

29. The pharmaceutical composition of any one of clauses 1 to 28, wherein the composition upregulates a Th-2 specific transcriptional factor.

30. The pharmaceutical composition of clause 29, wherein the Th-2 specific transcriptional factor is STAT-6.

31. The pharmaceutical composition of clause 29, wherein the Th-2 specific transcriptional factor is GATA-3.

32. The pharmaceutical composition of any one of clauses 1 to 31, wherein the composition is associated with a Th-2 bias in the Th-1/Th-2 balance.

33. The pharmaceutical composition of any one of clauses 1 to 32, for use in the treatment of multiple sclerosis.

34. The pharmaceutical composition of any one of clauses 1 to 33, wherein the composition reduces a symptom associated with multiple sclerosis.

35. The pharmaceutical composition of clause 34, wherein the symptom associated with multiple sclerosis is an inflammatory symptom.

36. A pharmaceutical composition comprising a polypeptide from about 6 to about 35 amino acid residues, the polypeptide comprising 1 to 3 tetrapeptides having the sequence of PEXP, wherein
P is proline;
E is glutamic acid; and
X is any amino acid.

37. The pharmaceutical composition of clause 36, wherein at least one tetrapeptide comprises the amino acid sequence of SEQ ID NO: 3.

38. The pharmaceutical composition of clause 36 or clause 37, wherein at least one tetrapeptide comprises the amino acid sequence of SEQ ID NO: 4.

39. The pharmaceutical composition of any one of clauses 36 to 38, wherein at least one tetrapeptide comprises the amino acid sequence of SEQ ID NO: 5.

40. The pharmaceutical composition of clause 36, wherein the polypeptide comprises the amino acid sequence of SEQ ID NO: 6.

41. The pharmaceutical composition of any one of clauses 36 to 40, wherein the polypeptide comprises a polyproline helical conformation.

42. The pharmaceutical composition of any one of clauses 36 to 41 further comprising a cell penetrating peptide.

43. The pharmaceutical composition of clause 42, wherein the cell penetrating peptide is selected from the group consisting of Penetratin, Pep-1, Pep-2, VP22, pVEC, pISL, hCT derived peptide, LL-37, Mouse PrP, Transportan, TP10, Arg11, MAP, MPG, KALA, ppTG1, and ppTG20.

44. The pharmaceutical composition of clause 42, wherein the cell penetrating peptide is a bipartite peptide (K16ApoE) consisting of a polylysine segment linked with the apolipoprotein-E peptide.

45. The pharmaceutical composition of clause 42, wherein the cell penetrating peptide is Pep-1.

46. The pharmaceutical composition of any one of clauses 36 to 45, wherein the composition suppresses p65 binding.

47. The pharmaceutical composition of any one of clauses 36 to 46, wherein the composition suppresses p65 activation.

48. The pharmaceutical composition of any one of clauses 36 to 47, wherein the composition inhibits NF-κB translocation to the nucleus of a cell.

49. The pharmaceutical composition of any one of clauses 36 to 48, wherein the composition suppresses T cell response.

50. The pharmaceutical composition of any one of clauses 36 to 49, wherein the composition suppresses T-bet transcription.

51. The pharmaceutical composition of any one of clauses 36 to 50, wherein the composition suppresses a pro-inflammatory cytokine.

52. The pharmaceutical composition of any one of clauses 36 to 51, wherein the composition suppresses a cytokine associated with Th-1 response.

53. The pharmaceutical composition of clause 52, wherein the cytokine is selected from the group consisting of IL-12, IL-17, IFN-γ, TNF-α, and IL-23.

54. The pharmaceutical composition of clause 52, wherein the cytokine is IL-12.

55. The pharmaceutical composition of clause 52, wherein the cytokine is IL-17.

56. The pharmaceutical composition of clause 52, wherein the cytokine is IFN-γ.

57. The pharmaceutical composition of clause 52, wherein the cytokine is TNF-α.

58. The pharmaceutical composition of clause 52, wherein the cytokine is IL-23.

59. The pharmaceutical composition of any one of clauses 36 to 48, wherein the composition enhances a cytokine associated with Th-2 response.

60. The pharmaceutical composition of clause 59, wherein the cytokine is selected from the group consisting of IL-4, IL-10 and TGF-β.

61. The pharmaceutical composition of clause 59, wherein the cytokine is IL-4.

62. The pharmaceutical composition of clause 59, wherein the cytokine is IL-10.

63. The pharmaceutical composition of clause 59, wherein the cytokine is TGF-β.

64. The pharmaceutical composition of any one of clauses 36 to 63, wherein the composition upregulates a Th-2 specific transcriptional factor.

65. The pharmaceutical composition of clause 64, wherein the Th-2 specific transcriptional factor is STAT-6.

66. The pharmaceutical composition of clause 64, wherein the Th-2 specific transcriptional factor is GATA-3.

67. The pharmaceutical composition of any one of clauses 36 to 66, wherein the composition is associated with a Th-2 bias in the Th-1/Th-2 balance.

68. The pharmaceutical composition of any one of clauses 36 to 67, for use in the treatment of multiple sclerosis.

69. The pharmaceutical composition of any one of clauses 36 to 68, wherein the composition reduces a symptom associated with multiple sclerosis.

70. The pharmaceutical composition of clause 69, wherein the symptom associated with multiple sclerosis is an inflammatory symptom.

71. A method of treating multiple sclerosis, the method comprising the step of administering to a patient in need thereof a therapeutically effective amount of the pharmaceutical composition of any one of clauses 1 to 70.

72. The method of clause 71, wherein the method suppresses p65 binding in the patient.

73. The method of clause 71 or clause 72, wherein the method suppresses p65 activation in the patient.

74. The method of any one of clauses 71 to 73, wherein the method inhibits NF-κB translocation to the nucleus of a cell in the patient.

75. The method of any one of clauses 71 to 74, wherein the method suppresses T cell response in the patient.

76. The method of any one of clauses 71 to 75, wherein the method suppresses T-bet transcription in the patient.

77. The method of any one of clauses 71 to 76, wherein the method suppresses a pro-inflammatory cytokine in the patient.

78. The method of any one of clauses 71 to 77, wherein the method suppresses a cytokine associated with Th-1 response in the patient.

79. The method of clause 78, wherein the cytokine is selected from the group consisting of IL-12, IL-17, IFN-γ, TNF-α, and IL-23.

80. The method of clause 78, wherein the cytokine is IL-12.

81. The method of clause 78, wherein the cytokine is IL-17.

82. The method of clause 78, wherein the cytokine is IFN-γ.

83. The method of clause 78, wherein the cytokine is TNF-α.

84. The method of clause 78, wherein the cytokine is IL-23.

85. The method of any one of clauses 71 to 84, wherein the method enhances a cytokine associated with Th-2 response in the patient.

86. The method of clause 85, wherein the cytokine is selected from the group consisting of IL-4, IL-10 and TGF-β.

87. The method of clause 85, wherein the cytokine is IL-4.

88. The method of clause 85, wherein the cytokine is IL-10.

89. The method of clause 85, wherein the cytokine is TGF-β.

90. The method of any one of clauses 71 to 89, wherein the method upregulates a Th-2 specific transcriptional factor in the patient.

91. The method of clause 89, wherein the Th-2 specific transcriptional factor is STAT-6.

92. The method of clause 89, wherein the Th-2 specific transcriptional factor is GATA-3.

93. The method of any one of clauses 71 to 92, wherein the method is associated with a Th-2 bias in the Th-1/Th-2 balance.

94. The method of any one of clauses 71 to 93, wherein the administration is an injection.

95. The method of clause 94, wherein the injection is selected from the group consisting of intraarticular, intravenous, intramuscular, intradermal, intraperitoneal, and subcutaneous injections.

96. The method of clause 94, wherein the injection is an intravenous injection.

97. The method of any one of clauses 71 to 96, wherein the administration is performed as a single dose administration.

98. The method of any one of clauses 71 to 96, wherein the administration is performed as a multiple dose administration.

99. A pharmaceutical formulation comprising the pharmaceutical composition of any one of clauses 1 to 70.

100. The pharmaceutical formulation of clause 99 further comprising a pharmaceutically acceptable carrier.

101. The pharmaceutical formulation of clause 99 or clause 100 optionally including one or more other therapeutic ingredients.

102. The pharmaceutical formulation of any one of clauses 99 to 101 wherein the formulation is a single unit dose.

103. A lyophilisate or powder of the pharmaceutical formulation of any one of clauses 99 to 102.

104. An aqueous solution produced by dissolving the lyophilisate or powder of clause 103 in water.

BRIEF DESCRIPTION OF THE DRAWINGS

FIG. 6 shows treatment with GILZ-peptide (GILZ-P) (SEQ ID NO: 6) suppresses proliferative responses and cytokine secretion by antigen primed T cells.

DETAILED DESCRIPTION OF THE ILLUSTRATIVE EMBODIMENTS

Figure 1:
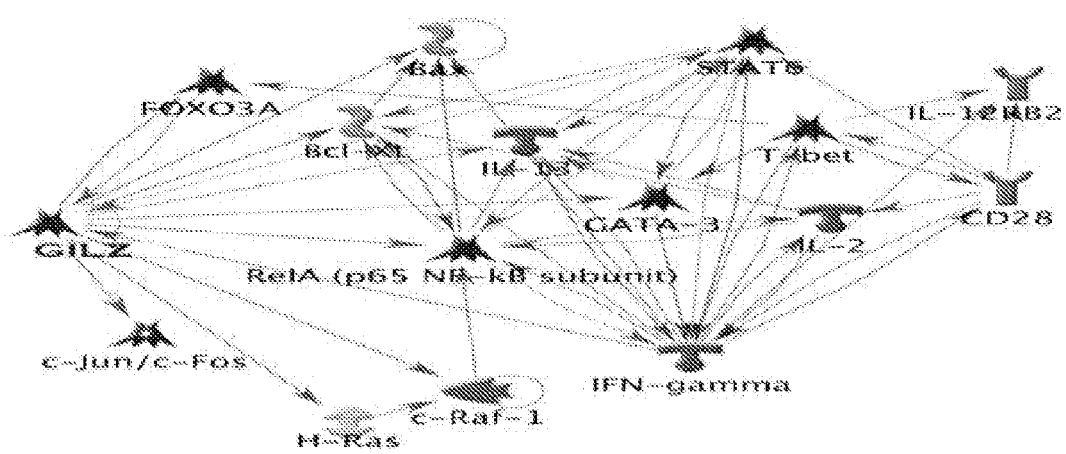
FIG. 1 shows pathways underlying functional influence are reconstructed in MetaCore. The network has 75% of its nodes associated with T cell mediate inflammatory diseases by annotations in MetaCore. GILZ was identified as a "divergence" hub functionally linked to multiple up/downstream target genes differentially expressed in activated CD4+ T cells. Functionally inhibitory and positive links are highlighted in red and green, respectively.

Various embodiments of the invention are described herein as follows. In one embodiment described herein, a pharmaceutical composition comprising a polypeptide from about 6 to about 35 amino acid residues is provided. As used herein, the term "about" means within a statistically meaningful range of a value or values such as a stated concentration, length, molecular weight, pH, sequence identity, time frame, temperature or volume. Such a value or range can be within an order of magnitude, typically within 20%, more typically within 10%, and even more typically within 5% of a given value or range. The allowable variation encompassed by "about" will depend upon its particular use under study, and can be readily appreciated by one of skill in the art. The polypeptide comprises 1 to 3 tetrapeptides having the sequence of PXXP, wherein P is proline, and X is any amino acid.

In another embodiment described herein, a pharmaceutical composition comprising a polypeptide from about 6 to about 35 amino acid residues is provided. The polypeptide comprises 1 to 3 tetrapeptides having the sequence of PEXP, wherein P is proline, E is glutamic acid, and X is any amino acid.

In various embodiments described herein, the pharmaceutical composition comprises a polypeptide wherein at least one tetrapeptide comprises the amino acid sequence of PEEP (SEQ ID NO: 3). In other embodiments described herein, the pharmaceutical composition comprises a polypeptide wherein at least one tetrapeptide comprises the amino acid sequence of PESP (SEQ ID NO: 4). In yet other embodiments described herein, the pharmaceutical composition comprises a polypeptide wherein at least one tetrapeptide comprises the amino acid sequence of PEAP (SEQ ID NO: 5).

In some embodiments described herein, the pharmaceutical composition comprises a polypeptide comprising the amino acid sequence of CLSPEEPAPESPQVPEAPGGSAV (SEQ ID NO: 6). In other embodiments described herein, the pharmaceutical composition comprises a polypeptide comprising the amino acid sequence of CSLPEEPAPEAPETPE-TPEAPGGSAV (SEQ ID NO: 7).

In some embodiments described herein, the pharmaceutical composition comprises a polypeptide from about 6 to about 35 amino acid residues. In other embodiments described herein, the pharmaceutical composition comprises a polypeptide from about 6 to about 30 amino acid residues. In yet other embodiments described herein, the pharmaceutical composition comprises a polypeptide from about 10 to about 30 amino acid residues. In one illustrative embodiment, the pharmaceutical composition comprises a polypeptide from about 6 to about 22 amino acid residues. In another illustrative embodiment, the pharmaceutical composition comprises a polypeptide from about 12 to about 30 amino acid residues. In another illustrative embodiment, the pharmaceutical composition comprises a polypeptide from about 12 to about 22 amino acid residues.

In various embodiments described herein, the pharmaceutical composition comprises a polypeptide wherein the polypeptide comprises a polyproline helical conformation. As used herein, the term "polyproline helical conformation" means a helical conformation of a peptide that is commonly associated with more than one proline residues.

In various embodiments described herein, the pharmaceutical composition further comprises a cell penetrating peptide (also known as a chariot peptide). Chariot and cell penetrating peptides are known by those of skill in the art. For review, see El-Andaloussi et al. (2005) *Current Pharm. Design* 11:3597-3611 and Wagstaff & Jans (2006) *Current Med. Chem.* 13:1371-1387. In some embodiments, the cell penetrating peptide is selected from the group consisting of Penetratin, Pep-1, Pep-2, VP22, pVEC, pISL, hCT derived peptide, LL-37, Mouse PrP, Transportan, TP10, Arg11, MAP, MPG, KALA, ppTG1, and ppTG20. In one illustrative embodiment, the cell penetrating peptide is a bipartite peptide (K16ApoE) comprising a polylysine segment linked with the apolipoprotein-E peptide. In another illustrative embodiment, the cell penetrating peptide is Pep-1.

In some embodiments, the pharmaceutical composition comprises a polypeptide that is protected from aminopeptidases and/or carbozypeptidases. In one illustrative embodiment, the polypeptide is amidated at the amino terminus and acetylated at the carboxy terminus.

In various embodiments described herein, the polypeptide can be modified by the inclusion of one or more conservative amino acid substitutions. As is well known to those skilled in the art, altering any non-critical amino acid of a peptide by conservative substitution should not significantly alter the activity of that peptide because the side-chain of the replacement amino acid should be able to form similar bonds and contacts to the side chain of the amino acid which has been replaced.

Non-conservative substitutions are possible provided that these do not excessively affect the p65 sequestering activity of the polypeptide and/or reduce its effectiveness in suppressing inflammatory cytokines.

As is well-known in the art, a "conservative substitution" of an amino acid or a "conservative substitution variant" of a peptide refers to an amino acid substitution which maintains: 1) the secondary structure of the peptide; 2) the charge or hydrophobicity of the amino acid; and 3) the bulkiness of the side chain or any one or more of these characteristics. Illustratively, the well-known terminologies "hydrophilic residues" relate to serine or threonine. "Hydrophobic residues" refer to leucine, isoleucine, phenylalanine, valine or alanine, or the like. "Positively charged residues" relate to lysine, arginine, ornithine, or histidine. "Negatively charged residues" refer to aspartic acid or glutamic acid. Residues having "bulky side chains" refer to phenylalanine, tryptophan or tyrosine, or the like. A list of illustrative conservative amino acid substitutions is given in TABLE 1.

TABLE 1

| For Amino Acid | Replace With |
|---|---|
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

In various embodiments described herein, the pharmaceutical composition suppresses p65 binding. In other embodiments described herein, the pharmaceutical composition suppresses p65 activation. In yet other embodiments described herein, the pharmaceutical composition inhibits NF-κB translocation to the nucleus of a cell.

In various embodiments described herein, the pharmaceutical composition suppresses T cell response. In other embodiments described herein, the pharmaceutical composition suppresses T-bet transcription.

In various embodiments described herein, the pharmaceutical composition suppresses a pro-inflammatory cytokine. In other embodiments described herein, the pharmaceutical composition suppresses a cytokine associated with Th-1 response. In some embodiments described herein, the cytokine is selected from the group consisting of IL-12, IL-17, IFN-γ, TNF-α, and IL-23. In one illustrative embodiment, the cytokine is IL-12. In another illustrative embodiment, the cytokine is IL-17. In yet another illustrative embodiment, the cytokine is IFN-γ. In another illustrative embodiment, the cytokine is TNF-α. In another illustrative embodiment, the cytokine is IL-23.

In various embodiments described herein, the pharmaceutical composition enhances a cytokine associated with Th-2 response. In some embodiments described herein, the cytokine is selected from the group consisting of IL-4, IL-10 and TGF-β. In one illustrative embodiment, the cytokine is IL-4. In another illustrative embodiment, the cytokine is IL-10. In yet another illustrative embodiment, the cytokine is TGF-β.

In various embodiments described herein, the pharmaceutical composition upregulates a Th-2 specific transcriptional factor. In one illustrative embodiment, the Th-2 specific transcriptional factor is STAT-6. In another illustrative embodiment, the Th-2 specific transcriptional factor is GATA-3.

In various embodiments described herein, the pharmaceutical composition is associated with a Th-2 bias in the Th-1/Th-2 balance.

In various embodiments described herein, the pharmaceutical composition is for use in the treatment of multiple sclerosis. In some embodiments described herein, the pharmaceutical composition reduces a symptom associated with multiple sclerosis. In one illustrative embodiment, the symptom associated with multiple sclerosis is an inflammatory symptom.

In another embodiment described herein, a method of treating MS is provided. The method comprises the step of administering to a patient in need thereof a therapeutically effective amount of any of the pharmaceutical compositions described herein.

As used herein, "treatment" of MS includes, but is not limited to, reduction or prevention of inflammation, inhibition of tissue damage, mitigation of clinical symptoms, and/or promotion of recovery following an acute episode.

Experimental autoimmune encephalomyelitis (EAE) is an animal model for human MS. blood-brain barrier. Recently, it has been reported that blockade of CD28:CD152/CD80 costimulation ameliorates EAE by suppressing NF-κB mediated inflammatory cytokines and upregulating GILZ expression in T cells (Dudhgaonkar et al., (2009) *Int Immunopharmacol*. (11):1272-80).

Without being bound by any particular theory, it is believed herein that GILZ mimetic polypeptides may inhibit the activity of NFκB and thereby suppress inflammatory cytokines. The inhibitory potential of the polypeptides is assessed by measuring the functional response of CD4+ T cells from mice induced with EAE to re-stimulation with the priming antigen in vitro in the presence/absence of GILZ/GILZ mimetics.

The previously described embodiments of the pharmaceutical compositions are applicable to the method described herein. In various embodiments, the administration according to the described methods is an injection. In some embodiments, the injection is selected from the group consisting of intraarticular, intravenous, intramuscular, intradermal, intraperitoneal, and subcutaneous injections. In one embodiment, the injection is an intravenous injection.

In other various embodiments, the administration according to the described methods is performed as a single dose administration. In other embodiments, the administration according to the described methods is performed as a multiple dose administration.

In yet other embodiments, pharmaceutical formulations are provided. In one illustrative embodiment, the pharmaceutical formulation comprises any of the pharmaceutical compositions described herein. The previously described embodiments of the pharmaceutical compositions are applicable to the pharmaceutical formulations described herein.

The type of formulation employed for the administration of the compounds may be dictated by the particular compounds employed, the type of pharmacokinetic profile desired from the route of administration and the compound(s), and the state of the patient. The polypeptides may be formulated as pharmaceutical compositions for systemic administration. Such pharmaceutical compositions and processes for making the same are known in the art for both humans and non-human mammals. See, e.g., Remington: The Science and Practice of Pharmacy, (A. Gennaro, et al., eds., 19$^{th}$ ed., Mack Publishing Co., 1995).

In some embodiments, the pharmaceutical formulations described herein further comprise a pharmaceutically acceptable carrier. In some embodiments, the pharmaceutical formulations described herein further comprise a pharmaceutically acceptable diluent. Diluent or carrier ingredients used in the pharmaceutical compositions containing polypeptides can be selected so that they do not diminish the desired effects of the polypeptide. Examples of suitable dosage forms include aqueous solutions of the polypeptides, for example, a solution in isotonic saline, 5% glucose or other well-known pharmaceutically acceptable liquid carriers such as alcohols, glycols, esters and amides.

As used herein, "carrier" refers to any ingredient other than the active component(s) in a formulation. Pharmaceutically acceptable carriers are determined in part by the particular composition being administered, as well as by the particular method used to administer the composition (see, e.g., Remington's Pharmaceutical Sciences, 17th ed. (1985)). The choice of carrier will to a large extent depend on factors such as the particular mode of administration, the effect of the carrier on solubility and stability, and the nature of the dosage form. In one illustrative aspect, the carrier is a liquid carrier.

As used herein, the term "pharmaceutically acceptable" includes "veterinarily acceptable", and thus includes both human and animal applications independently. For example, a "patient" as referred to herein can be a human patient or a veterinary patient, such as a domesticated animal (e.g., a pet).

In some embodiments, the pharmaceutical formulations described herein optionally include one or more other therapeutic ingredients. As used herein, the term "active ingredient" or "therapeutic ingredient" refers to a therapeutically active compound, as well as any prodrugs thereof and pharmaceutically acceptable salts, hydrates, and solvates of the compound and the prodrugs. Other active ingredients may be combined with the described polypeptides and may be either administered separately or in the same pharmaceutical formulation. The amount of other active ingredients to be given may be readily determined by one skilled in the art based upon therapy with described polypeptides.

In some embodiments, the pharmaceutical formulations described herein are a single unit dose. As used herein, the term "unit dose" is a discrete amount of the composition comprising a predetermined amount of the described polypeptides. The amount of the described polypeptides is generally equal to the dosage of the described polypeptides which would be administered to an animal or a convenient fraction of such a dosage such as, for example, one-half or one-third of such a dosage.

In one illustrative aspect, parenteral formulations may be suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art.

The aqueous preparations according to the invention can be used to produce lyophilisates by conventional lyophilization or powders. The preparations according to the invention are obtained again by dissolving the lyophilisates in water or other aqueous solutions. The term "lyophilization," also known as freeze-drying, is a commonly employed technique for presenting proteins which serves to remove water from the protein preparation of interest. Lyophilization is a process by which the material to be dried is first frozen and then the ice or frozen solvent is removed by sublimation in a vacuum environment. An excipient may be included in pre-lyophilized formulations to enhance stability during the freeze-drying process and/or to improve stability of the lyophilized product upon storage. For example, see Pikal, *M. Biopharm.* 3(9)26-30 (1990) and Arakawa et al., *Pharm. Res.,* 8(3):285-291 (1991).

In one embodiment, the solubility of the polypeptides used in the preparation of a parenteral formulation may be increased by the use of appropriate formulation techniques, such as the incorporation of solubility-enhancing agents.

In various embodiments, formulations for parenteral administration may be formulated to be for immediate and/or modified release. Modified release formulations include delayed, sustained, pulsed, controlled, targeted and programmed release formulations. Thus, a polypeptide may be formulated as a solid, semi-solid, or thixotropic liquid for administration as an implanted depot providing modified release of the active compound.

The formulations can be presented in unit-dose or multi-dose sealed containers, such as ampules and vials. The formulations can also be presented in syringes, such as prefilled syringes.

In various embodiments, the dosages of the polypeptides can vary significantly depending on the patient condition and the severity of the disease to be treated. The effective amount to be administered to a patient is based on body surface area, patient weight or mass, and physician assessment of patient condition.

Suitable dosages of the polypeptides can be determined by standard methods, for example by establishing dose-response curves in laboratory animal models or in humans in clinical trials. Illustratively, suitable dosages of polypeptides (administered in a single bolus or over time) include from about 1 pg/kg to about 10 µg/kg, from about 1 pg/kg to about 1 µg/kg, from about 100 pg/kg to about 500 ng/kg, from about 1 pg/kg to about 1 ng/kg, from about 1 pg/kg to about 500 pg/kg, from about 100 pg/kg to about 500 ng/kg, from about 100 pg/kg to about 100 ng/kg, from about 1 ng/kg to about 10 mg/kg, from about 1 ng/kg to 1 mg/kg, from about 1 ng/kg to about 1 µg/kg, from about 1 ng/kg to about 500 ng/kg, from about 100 ng/kg to about 500 µg/kg, from about 100 ng/kg to about 100 µg/kg, from about 1 µg/kg to about 500 µg/kg, or from about 1 µg/kg to about 100 µg/kg. In each of these embodiments, dose/kg refers to the dose per kilogram of a patient's or animal's mass or body weight.

EXAMPLE 1

Design of GILZ Mimetics

GILZ mimetics are designed based on the primary structure of GILZ, a glucocorticoid-inducible gene, and its interaction with the p65 subunit of NF-κB. A cost-effective hybrid approach that combines initial in-silico screening with subsequent cellular validation is used to identify functional GILZ mimetics. Since activated p65 is present only in stimulated cells treatment with GILZ mimetics is less likely to cause global immunosuppression. Importantly, the GILZ mimetics may circumvent the complications associated with the negative effects of glucocorticoid receptor mediated transactivation and transrepression of multiple genes that follows synthetic glucocorticoid treatment by sequestering the active p65 within the cytoplasm.

Studies using genetically engineered cells that over-express gilz suggest that the GILZ interacts physically with the p65 subunit of NF-κB and modulates its activation. As an initial strategy to delineate the effects of GILZ on primary T cell responses, publicly available relevant microarray datasets were analyzed. The following were downloaded from the gene expression omnibus (GEO) database: the microarray datasets of CD3 activated T cells in the presence (GSE 6888) or absence of costimulation (GSE 5960) and Th1 clone or T-cell lymphoblastic lymphoma cell line treated with dexamethsone for 3 hrs (GSE 5463) or 24 hrs (GSE 7067) respectively. Bioinformatic analyses were performed using the MetaCore™ software package (http://portal.genego.com). Comparative analyses after normalization of differentially expressed genes showed that while both anergic T cells and dexamethasone treated T cells expressed GILZ, it was significantly upregulated in the later cells. Enrichment of functional processes was calculated by "GeneGo process networks" using a threshold of 0.001 and a false discovery rate <5%. Although GILZ was present in anergic T cells and in dexamethasone treated cells, its expression level did not reach the threshold set for statistical significance in the enrichment analysis. Hence GILZ was added manually to the immune response processes prior to building networks. GILZ was identified as a "divergence" hub functionally linked to multiple genes differentially expressed in activated CD4+ T cells. Interactome analysis revealed that while the pro-inflammatory factors T-bet, IFN-γ and TNF-αinhibit GILZ; anti-inflammatory factors GATA-3 and IL-13 are activated by GILZ (see FIG. 1). GILZ mediated inhibition of anti-apoptotic factor, Bcl-XL, may indicate a potential role for GILZ in the deletion of activated T cells. Since many of these mechanisms occur following NF-κB transactivation, an important role played by GILZ may reside in its ability to prevent nuclear translocation of the p65 subunit of NF-Kβ (see FIG. 1).

The primary sequence of GILZ is homologous with that of the evolutionarily conserved TGF β-stimulated clone 22 gene (TSC-22) and porcine delta sleep inducing peptide (DSIP). They share the leucine-zipper (LZ) motif commonly found in transcriptional regulatory proteins and a proline rich carboxy (COOH) terminus. Solution structure suggested that while the LZ motif of DSIP adopts helical conformation, the proline rich COOH region is more flexible. This is consistent with the observations that the LZ domains facilitate dimerization and the flexible proline rich regions participate in protein-protein interactions.

Structurally, p65 possesses a rel homology domain (RHD), a nuclear localization sequence (NLS) masked in resting cells by the IκB inhibitory proteins and carboxy terminal transactivation domains (TAD). The TAD-1 (residues 521-551) is the dominant contributor to the transactivation activity of p65. The GILZ: p65 interaction is independent of IκB phosphorylation and the release of p65 from the IκB inhibitory complex. This suggests that the interaction does not involve the RHD or NLS regions, and that the GILZ binds the TAD of p65. Manipulation of interactions of p65-TAD with other proteins modulates its transactivation ability.

Mutational analyses have localized the p65 binding site to the proline rich COOH terminus of GILZ. Proline rich sequences are commonly found in interfaces of transient protein-protein interactions, where proline provides the rapid kinetics and the adjacent residues contribute to the specificity of the interactions.

The sequence of proline rich human GILZ-COOH is identical with that of the TSC22 and the DSIP. Homology models of GILZ mimetics are built using the solution structure of DSIP (PDB: 1DIP) as the template by modeling programs (e.g. Geno 3D/SWISS MODEL). The structure of the predicted models is refined by energy minimization and removal of unfavorable bond geometry. Since the conformation of proline rich regions in proteins are locally driven with little/ no involvement of long-range interactions and the GILZ-mimetics are designed by rational substitutions in the proline rich GILZ-WT (SEQ ID NO: 2), the GILZ mimetics may retain a structural representation with reference to the adjacent residues and adopt a similar conformation as wild type GILZ.

GILZ-mimetics are superimposed over the carboxy terminal region of the predicted GLIZ model and PDB: 1DIP. GILZ mimetics within 5 Å RMSD when superimposed over both are selected for in silico docking NMR studies suggest that the 133 residue TAD of p65 adopts α-helical conformation facilitated by the Asp/Glu rich domain. A structure homology search revealed similarity between the acidic activation domain of the elongation factor eEF3 (PDB: 3H7H) and the TAD of p65. In addition, repositories in the public domain include multiple models of human p65 generated by homology-modeling. These models are used to evaluate the p65 binding potential of GILZ mimetics using a soft docking algorithm implemented in BiGGER (Biomolecular Complex Generation with Global Evaluation and Ranking). The coordinates of GILZ mimetics are systematically rotated in discrete steps and translated against the surface of human p65 TAD. In general two proteins are considered in contact with each other if the distance between the Cβ atoms is <5 Å. Top ranked GILZ mimetics within 5 Å distance of the residues critical for transactivation of p65 ($Asp^{533}$, $Asp^{541}$, $Ser^{536}$, $Phe^{542}$ and $Ser^{547}$) are selected for further analysis. Selected GILZ mimetics may be synthesized as peptide amides and amino terminal acetylation to minimize charge-helix dipole interaction and enhance helical stability.

Secondary Structure Analysis of GILZ Mimetics

Proline rich regions in polypeptides involved in transient protein-protein interactions often assume an extended helical conformation. The secondary structure and the binding kinetics between the GILZ protein/GILZ mimetics and the p65 protein are determined by circular dichroism and BIAcore analysis, respectively (Srinivasan et al. (2001) *J Immunol.* 167(1):578-85; Srinivasan et al., (2005) *J Biol Chem.* 280 (11):10149-55).

Circular dichroism (CD) measurements of the synthesized GILZ mimetics are recorded to demonstrate the secondary structure of GILZ mimetics in solution. Mimetics with defined extended helical conformation may be chosen for further functional characterization.

Binding of GILZ Mimetics

The direct interaction between the purified human GILZ and the purified or cellular p65 protein was studied using a modified ELISA. The human GILZ-GST protein and the anti-human GILZ mAb were purchased from Abnova, Teipie City, Taiwan. Purified human p65 protein and the anti-human p65 mAb were from Active Motif, Carlsbad Calif.

Isolation and Culture of Peripheral Blood Mononuclear Cells (PBMC)

PBMC isolated from 10 cc blood of a healthy donor [vaccinated with the *Mycobacterium bovis* bacille Calmette-Guerin (BCG)] were cultured in complete RPMI at 1×105 cells/well and stimulated with purified protein derivative [PPD:10TU (tuberculin units)/ml] in the presence or absence dexamethasone (100 μm/ml). CD4+ T cells were isolated 24 and 48 hrs later by magnetic separation and cytoplasmic and nuclear fractions extracted for binding analysis. The protocol was approved by the Indiana University Human Studies Committee, Institutional Review Board.

GILZ:p65 Binding Analysis

To detect direct interaction, ELISA plates were coated with increasing concentrations of the GILZ protein and probed with increasing concentrations of the p65 protein followed by detection with anti-human GILZ mAb. To detect binding of cellular GILZ and p65, ELISA plates were coated with the p65 protein (20 ng), and probed with the cytoplasmic fraction from T cells. Binding of the plate bound p65 with the cytoplasmic GILZ protein was detected with anti-human GILZ mAb. Alternatively, wells coated with the GILZ-GST protein (20 ng) were probed with the nuclear fractions from T cells and the GILZ:nuclear p65 binding was detected with anti-human p65 mAb. The bound complex was detected with TNB at absorbance of 450 nm.

Results

Figure 2A:
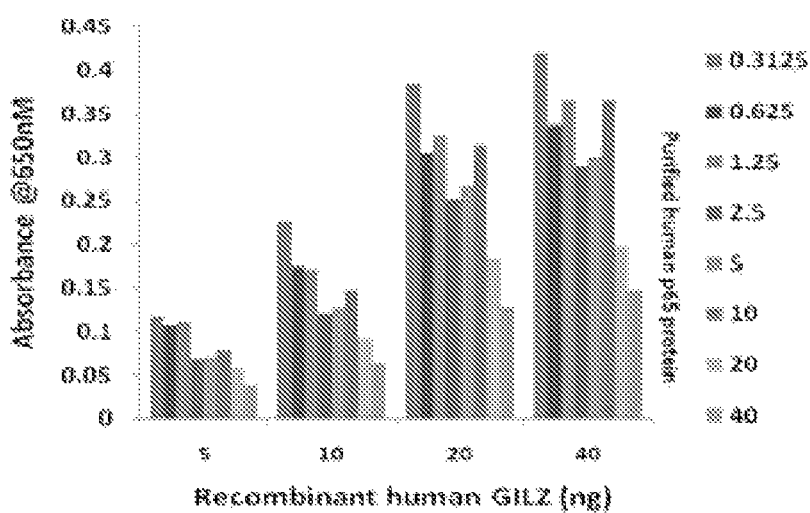
FIG. 2 shows GILZ:p65 binding analysis by ELISA. Wells coated with human GILZ protein at increasing concentrations (5-40 ng), were probed with recombinant p65 protein at increasing concentrations (0.3125-40 ng) and detected with anti-human GILZ mAb (A). Human CD4+ T cells were stimulated with PPD in the presence or absence of dexamethasone. ELISA plates coated with recombinant human p65 protein (B) or human GILZ protein (C) were probed with T cell cytoplasmic fractions (B) or nuclear fractions (C). The GILZ:p65 binding was detected with anti-human GILZ mAb (B) or anti-human p65 mAb (C). *=$p<0.05$ when compared to cells +PPD.

The GILZ:anti-GILZ complex formation was inhibited by p65 as evidenced by the decreasing absorbance with increasing concentration of the p65 protein (see FIG. 2A). The interaction appears to be non-linear with optimal binding at 1:4 ratio of p65 to GILZ proteins. Absorbance over the background was not observed in wells coated with anti-human GILZ mAb, probed with purified p65 and detected with anti-human p65 mAb. The absorbance was highest in wells probed with anti-GILZ mAb alone.

Figure 2B:
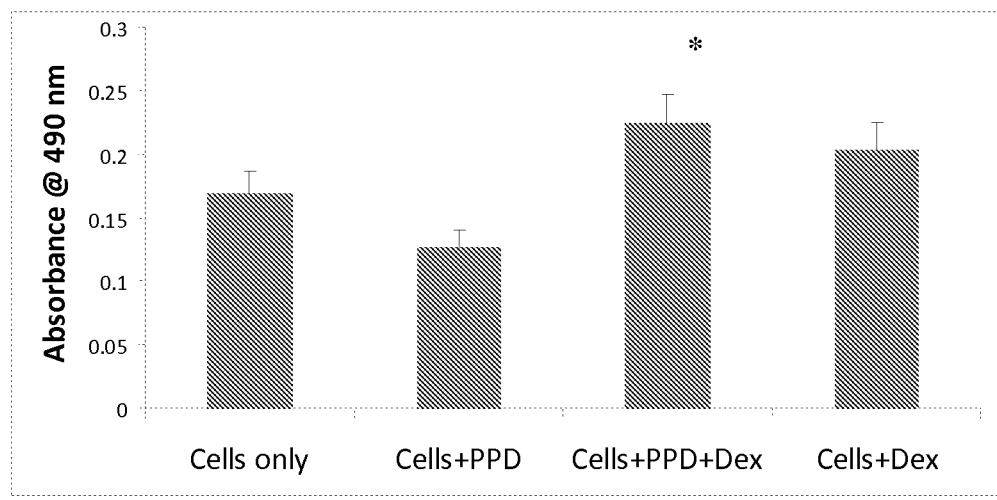
Figure 2C:
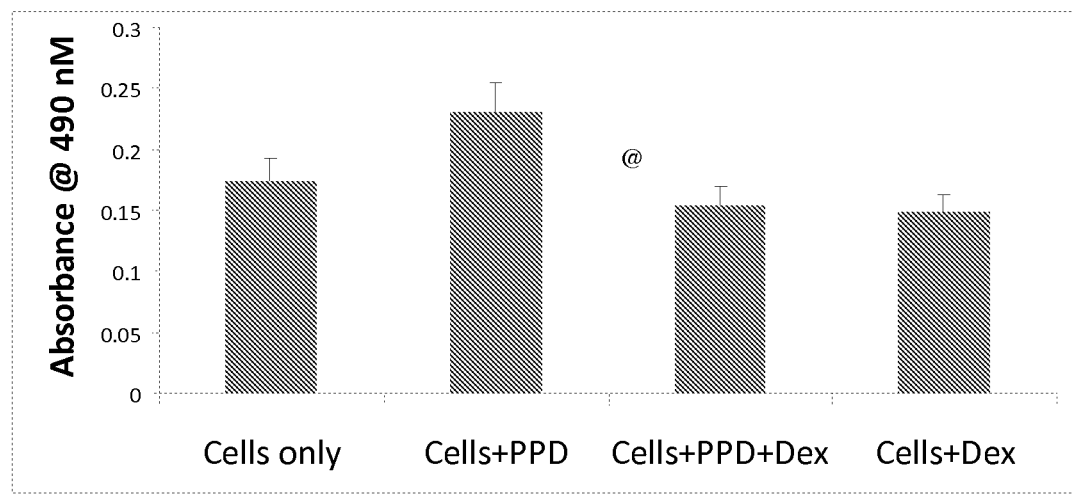

While T cell activation decreases GILZ expression, treatment of activated T cells with dexamethasone upregulates GILZ expression. Consistent with this increased absorbance in p65 coated wells probed with the cytoplasmic fraction of antigen activated CD4+ T cells treated with dexamethasone as compared with that from untreated cells was observed (see FIG. 2B). Activated T cells express increased p65 in the nucleus. Consistently, the absorbance was significantly decreased in wells coated with purified human GILZ protein and probed with the nuclear fraction of antigen stimulated cells treated with dexamethasone as compared to that from untreated cells (see FIG. 2C). Reduced p65 in nuclear fractions of cells treated with dexamethasone alone is consistent with the ability of glucocorticoids to inhibit NF-κB translocation in unstimulated cells also (see FIG. 2C). Results represent mean absorbance of three independent experiments.

Kinetics of GILZ Mimetics

In order to determine the kinetics of interaction between the two proteins BIAcore experiments are performed. BIAcore measures surface plasmon resonance (SPR) for real-time monitoring of intermolecular interactions. Functional GILZ-mimetics may bind the p65 protein with similar kinetics as wild type GILZ. Both direct and competitive kinetics for the interactions between the human GILZ protein/select GILZ mimetics and the human p65 protein are determined.

Experimental Design

Direct Kinetic Analysis

Purified p65 protein is immobilized on a CM-5 sensor chip using the amine coupling method as described. Human GILZ protein or GILZ mimetics at varying concentrations are injected as analytes. The binding is monitored in real time in terms of response units and the p65 surface regenerated between injections.

For competitive kinetic analysis, anti-human p65 or purified human GILZ protein are immobilized on the CM-5 sensor chip. Mixtures of purified human p65 protein with increasing concentrations of each GILZ mimetic are injected as analytes. The binding is monitored in real time in terms of response units and the bound protein regenerated between injections by washing with 5 mM NaOH. Data from the sensograms is analyzed to calculate the binding kinetics and affinity constant for the interaction using BIAevaluation and BIAsimulation software.

Figure 3A:
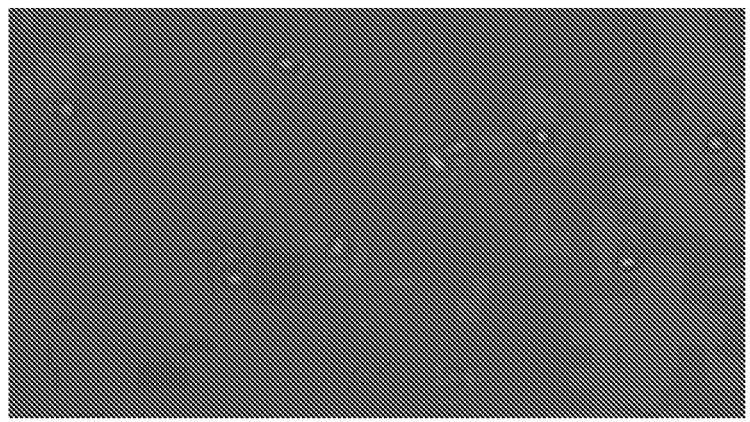
FIG. 3 shows intracellular delivery of GILZ protein. CD4+ T cells were permeabilized and incubated with human GILZ protein alone (B) or in 1:20 (molar concentration) GILZ: chariot peptide pre-formed complex (C) or left untreated (A). Intracellular delivery of GILZ protein was detected with fluorescently labeled anti-human GILZ mAb.
Figure 3B:
Figure 3C:
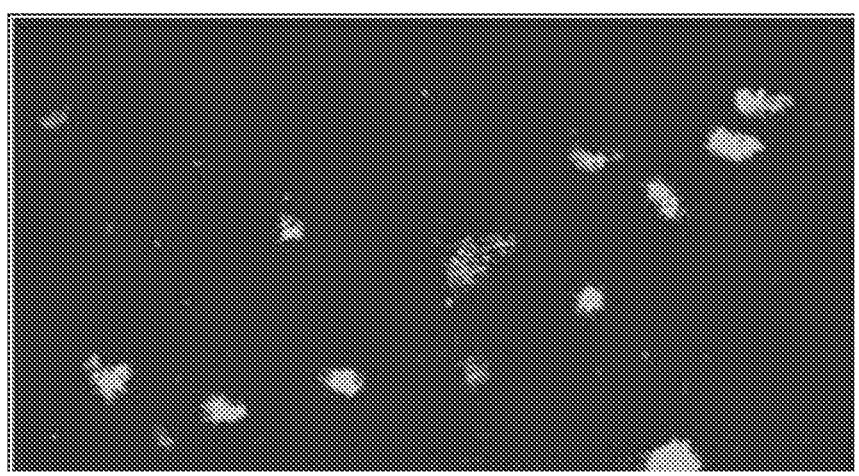

Functional Potential of GILZ Mimetics: Preliminary Studies to Test if Exogenous GILZ can Inhibit T Cell Responses Gilz overexpressing transgenic mice exhibit reduced T-bet expression and IFN-γ secretion, a canonical Th1 transcription factor and prototype Th1 (pro-inflammatory) cytokine respectively. In contrast GILZ expression upregulates transcriptional factors associated with Th2 (anti-inflammatory) differentiation including STAT-6 and GATA-3 and increase IL-4 secretion, a prototype Th2 cytokine GILZ may regulate immune response by modulating the Th1/Th2 balance. The effect of intracellular delivery of GILZ protein on cytokine response was assessed in a delayed type hypersensitivity (DTH) reaction, a prototype Th1 response similar to the T cell responses in EAE/MS (see FIG. 3).

Initially, the effect of human GILZ protein was investigated on the responses of PBMC stimulated with PPD, a mycobacterial antigen, a method often used to investigate DTH responses. To obtain effective intracellular concentration, GILZ or GILZ mimetics were mixed with an amphipathic chariot peptide Pep-1 (Anaspec, San Jose, Calif.) which rapidly associates through hydrophobic non-covalent interactions and forms stable nanoparticle complexes in solution independent of cargo sequence or size. This is in contrast to a commonly used cell penetrating peptide, the transactivator (TAT) protein of the human immunodeficiency virus which requires direct coupling with the cargo for effective cellular import.

Isolation and Culture of Human CD4+ T Cells

Figure 4:
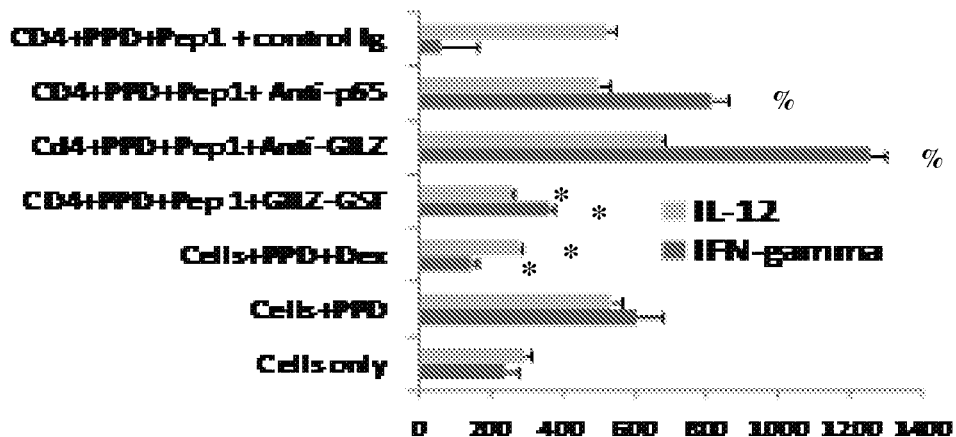
FIG. 4 shows exogenous GILZ suppressed Th1 cytokines. Human CD4+ T cells were stimulated with PPD alone or in the presence indicated agents as described above. Controls shown include untreated cells and cells treated with carrier peptide alone. Supernatant collected at 24 h post-stimulation was used to measure IFN-γ (A), IL-12 (B), TNF-α(CO and IL-10 (D) by ELISA. *=$p<0.05$ compared to cells stimulated with PPD alone and %=$p<0.05$ compared to untreated cells.
Figure 4:
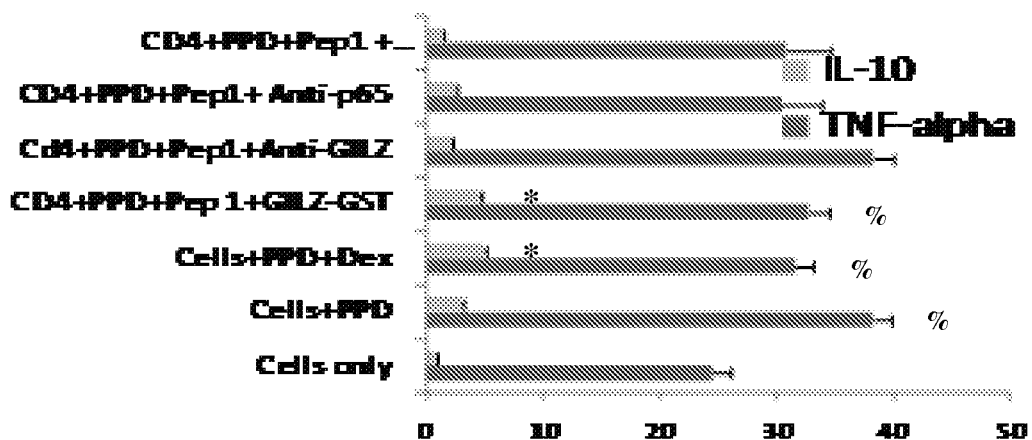

Purified CD4+ T cells isolated from PBMC by magnetic cell separation (Miltenyi Biotech, Germany), were seeded with irradiated autologous PBMC (T cells depleted) as APC at 1:1.5 ratio in serum-free RPMI (with 5% penicillin/streptomycin), and stimulated with PPD (20 μm/ml) alone or in the presence of dexamethasone (100 μm/ml) or 20:1 M complex of chariot peptide with GILZ protein (0.7 μm/ml)/anti-human GILZ mAb (1 μm/ml)/anti-human p65 mAb (1 μm/ml)/control antibody (1 μm/ml). Supernatants collected at 24 hrs were assessed for cytokines including human IFN-γ, TNF-α, IL-12 p40 and IL-10 using BD OptEIA™ kits. Differences in the secretion of cytokines between the groups were determined by one way ANOVA followed by Tukey's post-hoc analysis (see FIG. 4).

Results

While secretion of IFN-γ and IL-12 was significantly reduced, the IL-10 secretion was significantly elevated in PPD stimulated T cells treated with dexamethasone or exogenous GILZ protein (see FIG. 4A, FIG. 4B). The dexamethasone mediated inhibition of IFN-γ and IL-12 secretion or elevation of IL-10 was abrogated in cells concomitantly treated with anti-human GILZ mAb or anti-human p65 mAb (see FIG. 4A, FIG. 4B). The TNF-α secretion was not significantly altered between different treatments (see FIG. 4B). The cytokine secretions in PPD stimulated T cells treated with peptide carrier alone/peptide carrier and non specific immunoglobulin did not vary significantly from that of PPD stimulated cells. Cytokine secretion was not significant in unstimulated cell cultures in all conditions.

NF-κB is integrally involved in the transcriptional upregulation of multiple proinflammatory cytokines including IFN-γ and IL-12, that mediate tissue destruction in MS. Exogenous GILZ has been shown to suppress Th1 cytokines The ability of GILZ mimetics to inhibit NF-κB translocation and suppress T cell responses is assessed in EAE, a well established model for MS.

Induction and Analysis of EAE

Relapsing remitting EAE is induced in 8-10-week old female SJL/J mice. The mice were immunized with 100 µg of $PLP_{139-151}$ in PBS emulsified 1:1 in complete Freund's adjuvant supplemented with 200 µg of *Mycobacterium tuberculosis* H37RA (Difco Laboratories, Detroit, Mich.) distributed over four sites on the lateral hind flanks subcutaneously. Mice were injected with 100 ng of pertussis toxin (List Biological Laboratories, Campbell, Calif.) intraperitoneally on the day of immunization and 2 days later (Srinivasan et al., (2002) *J Immunol,* 169(4):2180-8).

T Cell Assays

Proliferative responses of CD4+ lymph node cells and splenocytes harvested 10 days post-induction upon re-stimulation in vitro with $PLP^{139-151}$ in the presence or absence of chariot peptide complexed with purified GILZ protein and/or GILZ mimetics at varying concentrations is determined as described. IL-2, TNF-α, IFN-γ, IL12-p40, IL-17, IL-4, IL-5, IL-10 and TGF-β) of the cells following similar in vitro restimulation is determined by ELISA. Measurement of relative quantities of Th1 and Th2 specific transcription factors is determined by real time PCR using ABI primers.

NF-κB Activation Assay

Nuclear and cytoplasmic protein fractions of CD4+ T cells obtained using a nuclear extraction kit are assessed for NF-κB activation and p65 nuclear translocation using Trans$^{AM}$ NF-κB kits (Active Motif, Carlsbad, Calif.). The effect of exogenous GILZ and GILZ mimetics on phosphorylation and proteolytic degradation of IκB proteins is determined by Western blot analysis of nuclear and cytoplasmic protein fractions from CD4+ T cells pretreated with GILZ/chariot peptide complex prior to stimulation.

TUNEL Assay

The effect of exogenous GILZ and GILZ mimetics on apoptosis is assessed by in situ cell death detection kit (Roche Applied Science, Indianapolis, Ind.). Briefly, $1 \times 10^6$ CD4+ T cells are preincubated with varying concentrations of GILZ protein/GILZ mimetic/chariot peptide complex and then stimulated with PPD (20 µg/ml) for 16 hrs. Fixed and permeabilized cells are probed with fluorescently labeled cell death detection reagent. Stained cells are analyzed using FACS-Calibur (BD Biosciences, CA).

Figure 5:
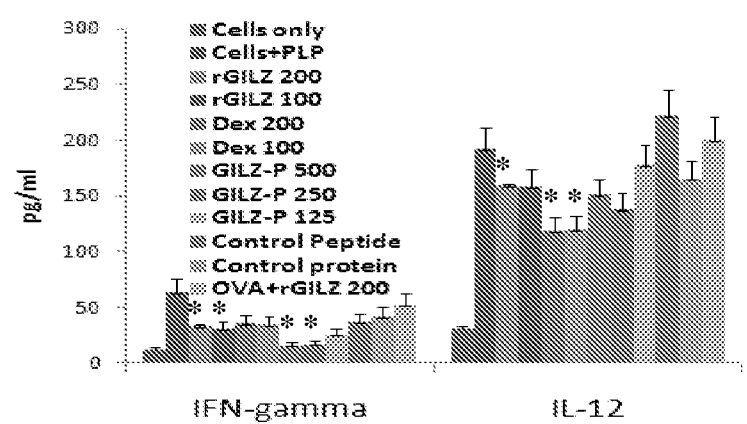
FIG. 5 shows treatment with rGILZ or wild type GILZ-peptide (GILZ-P) suppresses cytokine secretion by in-vivo primed T cells. CD4+ splenocytes isolated 10 days post-immunization from SJL mice induced EAE were co-cultured with irradiated syngenic APC and restimulated with PLP (40 µg/ml) in the presence of complex of chariot peptide with rGILZ protein/dexamethasone/GILZ-P at indicated concentrations. Supernatants collected after 24 hrs were assessed for INF-γ and IL-12p40 by ELISA. *=$p<0.05$ when compared to cells +PLP.

Previously, a peptide derived from the TAD1 of p65 has been shown to suppress TNF-αinduced NF-κB activation by preventing nuclear translocation of p65. GILZ has been shown to bind p65 in the cellular cytoplasm and inhibit its nuclear translocation. Human GILZ and the mouse GILZ share identical proline rich regions. Treatment with GILZ mimetics may inhibit NF-κB activation, T-bet transcription, and reduce pro-inflammatory cytokine secretion (see FIG. 5) to suppress antigen activated T cells in EAE. Activated NF-κB is expected to be lower in cells treated with exogenous GILZ. Multiple reports suggest that the NF-κB mediates suppression of apoptosis. Exogenous GILZ and GILZ mimetics may suppress NF-κB translocation and hence increase apoptosis of activated CD4+ T cells.

Peptide Synthesis

A 22 residue synthetic peptide derived from the carboxy terminus of murine GILZ having the amino acid sequence CLSPEEPAPESPQVPEAPGGSAV (SEQ ID NO: 6) (corresponding to 112C-V134 of GILZ and hereinafter "GILZ-WT or GILZ-P", was commercially synthesized as a peptide amide with amino terminal acetylation (Srinivasan et al., (2001) *J Immunol,* 167(1):578-85). Purity of the peptide was confirmed by matrix-assisted laser desorption/ionization time-of-flight mass spectrometry. A control peptide composed of randomly scrambled sequence of the GILZ-peptide was synthesized similarly.

Intracellular Delivery

For in vitro assays, dexamethasone/GILZ peptide/recombinant GILZ protein (r-GILZ) (Abnova, Teipie City, Taiwan)/ control peptide was incubated with the amphipathic chariot peptide (Pep-1) at 1:20 M ratio for 20 mins at room temperature before adding to the cell cultures (Deshayes et al., (2010) *Biochim Biophys Acta,* 1798(12):2304-14).

In Vitro Proliferation and Cytokine Assays

CD4+ lymph node cells (LNC) isolated from the draining lymph nodes harvested from SJL/J mice 10 days after immunization with $PLP_{139-151}$ were cultured in 96-well plates at $5 \times 10^6$ cells/well in complete RPMI and restimulated with the PLP peptide (40 µg/ml) for 72 h, including a final 16-h pulse with [$^3$H]-thymidine. Cultures contained dexamethasone ($10^{-7}$M)/different concentrations of GILZ peptide (125 µM-500 µM)/r-GILZ (100 ng & 200 ng)//Pep-1 (0.3 µM) in triplicate wells. Separate cultures stimulated with ova (40 µg/ml) served as control for antigen specificity. Irradiated splenocytes from syngenic mice were used as antigen presenting cells (APC). Cultures were harvested onto glass fiber mats using a Skatron harvester (Skatron, Sterling, Va.), and the levels of [$^3$H]-thymidine incorporation were determined by liquid scintillation counting (Microbeta; Wallac, Turku, Finland). Results were confirmed by replicate experiments. Data are expressed as Δcpm (counts/min incorporated in antigen-stimulated culture-counts/min incorporated by control unstimulated culture).

Supernatants from separate CD4+LNC cultured similarly collected at 24 hrs and 48 hrs were stored at −20° C. The levels of cytokines, IL-10, IL-12, and interferon gamma (IFN-γ) were determined by ELISA, using OptEIA kits, according to the manufacturer's recommendations (BD PharMingen). Group comparisons were made by one way analysis of variance (ANOVA) followed by Tukey's post-hoc.

Results

Figure 6A:
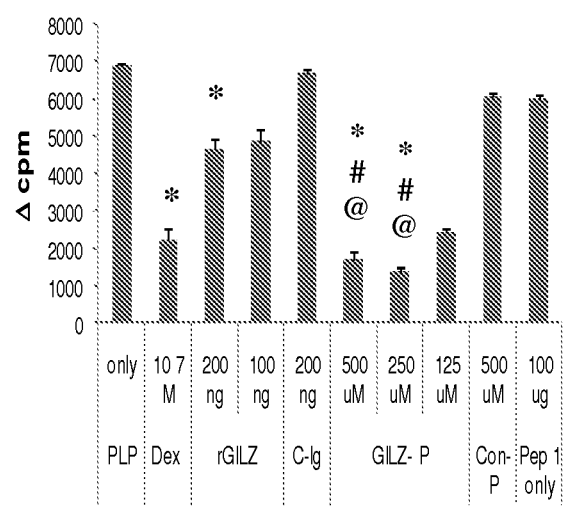
FIG. 6A shows single cell suspensions of $CD4^+$ LNC ($5\times10^5$ cells/well) isolated from SJL mice 10 days post-PLP immunization were co-cultured with irradiated syngenic APC and restimulated with PLP (40 µg/ml) for a total of 72 h (including an 18-h pulse with [$^3$H]-thymidine) in the presence of indicated concentrations of dexamethasone ($10^7$M)/GILZ peptide (125-500 µM)/control peptide(C-P)(500 µM)/r-GILZ (100-200 ng)/control-Ig (C-Ig) as shown. Cultures stimulated with ova (40 µg/ml) were included as control for antigen specificity (data not shown). Data are plotted as mean Δcpm (cpm of the antigen-stimulated cells-cpm of cells only) +/−SD. Results are the mean of three different experiments.

The inhibitory potential of GILZ peptide in in vitro functional assays was investigated. CD4+LNC from in vivo primed mice re-stimulated with PLP in the presence of dexamethasone (Δcpm: 2226+/−327)/GILZ peptide (500 µM Δcpm: 1702+/−217)/r-GILZ (200 ng Δcpm: 4658+/−266) exhibited significantly reduced proliferative responses as compared with LNC stimulated with PLP alone Δcpm: 6903+/−36). Cultures treated with GILZ peptide exhibited greater inhibition than those treated with r-GILZ at all concentrations. No significant inhibition was observed in PLP stimulated cultures treated with control peptide (Δcpm: 6079+/−70)/control Ig (Δcpm: 6663+/−118)/Pep-1 alone (Δcpm: 6022+/−87)/GILZ peptide in the absence of Pep-1 Δcpm 6663+/−173). LNC from PLP primed mice did not exhibit significant response to an irrelevant antigen, ova (Δcpm: 418+/−24) (see FIG. 6A).

Figure 6B:
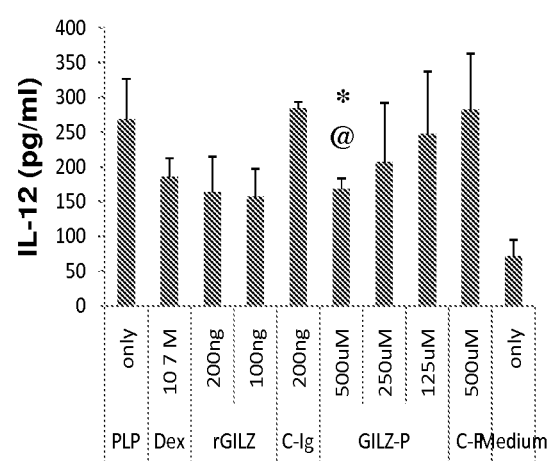
FIGS. 6B-D shows $CD4^+$ LNC from PLP-primed mice were restimulated with the immunogen in the presence of r-GILZ/GILZ peptide/control peptide/control Ig at indicated concentration. Supernatants collected 48 h later were assessed for IL-12 (B), IFN-γ (C) and IL-10 (D) by ELISA. Data are presented as mean+/−SD., # and @ $p<0.05$ as compared with the cells treated with PLP alone or cells stimulated in the presence of control peptide/control Ig respectively.
Figure 6C:
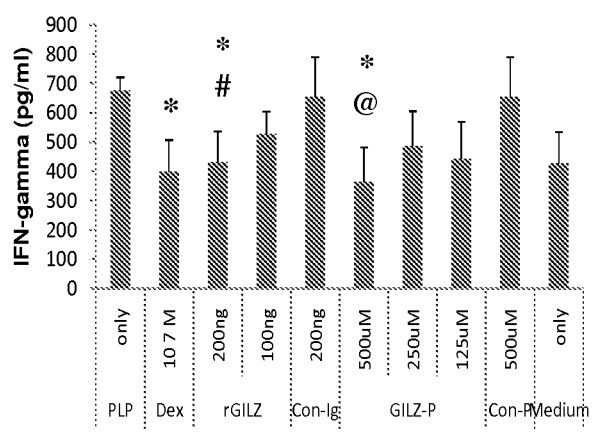
Figure 6D:
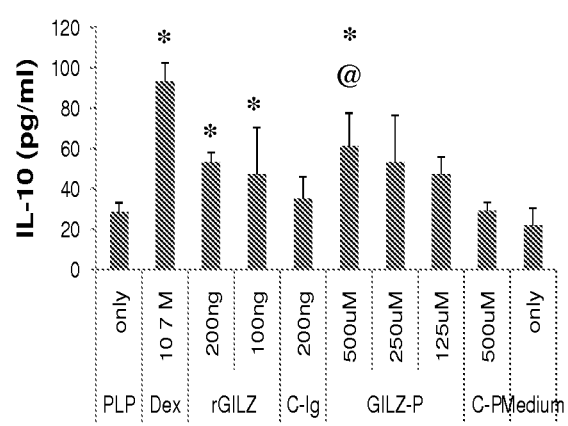

Draining LNC from PLP primed mice re-stimulated with antigen in-vitro and treated with dexamethasone/GILZ-peptide/r-GILZ at all concentrations secreted significantly decreased levels of IFN-γ (see FIG. 6B) and IL-12 (see FIG. 6C) but elevated levels of IL-10 (see FIG. 6D) than the untreated cells or LNC stimulated in the presence of control-Ig or control peptide (see FIGS. 6B-D).

These experiments demonstrate that exogenous GILZ protein or GILZ peptide can suppress antigen specific T cell proliferation. Previously, targeted silencing of GILZ has been shown to suppress proliferation of mitogen activated primary T cells. Treatment with the GILZ peptide or protein suppressed pro-inflammatory/Th1 cytokines and upregulated anti-inflammatory/Th2 cytokine Consistent with this observation, over-expression of GILZ in CD4+ T cells in transgenic mice has been shown to induce IL-4 and inhibit IFN-γ production, thereby down-regulating the Th-1 and upregulating the Th-2 response.

Effects of GILZ-Peptide Treatment on Relapsing Remitting EAE

As opposed to the B10.PL mice which often develop monophasic EAE, $PLP_{139-151}$ immunized SJL/J mice develop relapsing remitting form of EAE (R-EAE) (Dudhgaonkar et al. (2009) *J Immunol*, 183(11):7505-13). Groups of SJL/J mice were induced EAE as described above. Animals were observed daily for clinical signs and scored as follows: 0, no clinical signs; 1, limp tail or waddling gait with tail tonicity; 2, waddling gait with limp tail (ataxia); 2.5, ataxia with partial paralysis of one limb; 3, partial hind-limb paralysis; 3.5, full paralysis of one limb with partial paralysis of the second limb; 4, full paralysis of two limbs; 4.5 moribund; and 5, death (1, 8). For treatment of EAE, mice were administered intraperitonealy r-GILZ (2 ng/mouse) (Abnova, Teipie City, Taiwan) or GILZ peptide (GILZ-P) (SEQ ID NO: 6) or control peptide (500 μg/mouse) mixed with Pep1 (0.3 μM/mouse) in 100 μl PBS on the day of immunization. A group of mice received the GILZ peptide:Pep-1 complex on day 12 post-immunization. Groups of mice treated with PBS (vehicle) or Pep-1 alone were included as control.

In Vitro Proliferation and Cytokine Assays

Draining LNC isolated from mice induced R-EAE and treated with GILZ peptide/r-GILZ/control Ig/control peptide/Pep-1 alone or left untreated (vehicle) 45 days after disease induction were re-stimulated in vitro with PLP (40 μg/ml) or myelin basic protein peptide ($MBP_{87-99}$) (40 μg/ml) or both PLP and MBP (40 μg/ml each) or ova (40 μg/ml) and cultured as described. Supernatants collected 48 hrs later were assessed for cytokines using Opt EIA kits according to the manufacturer's recommendations (BD PharMingen). Differences between the groups in the mean clinical score and cytokine secretion were determined by a one-way ANOVA with Tukey's posthoc. Results were considered significant at $p<0.05$.

Results

Figure 7:
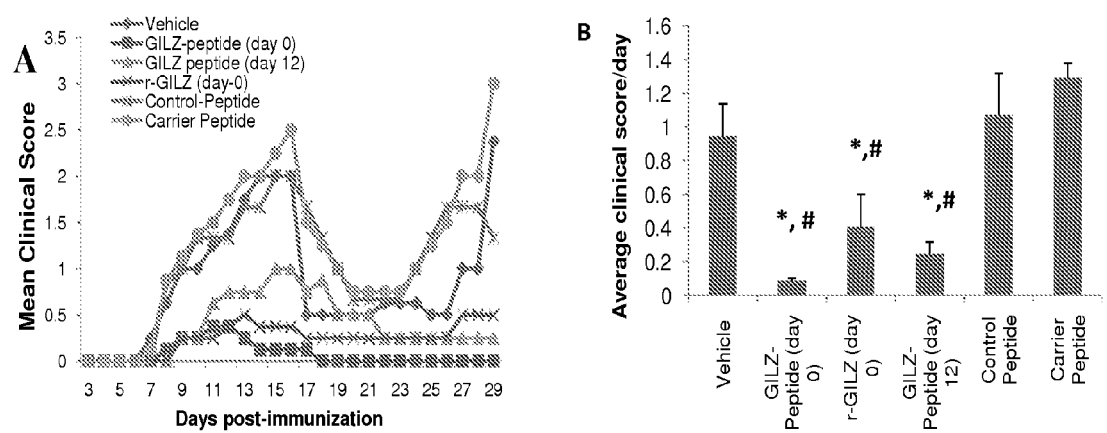
FIG. 7 shows GILZ peptide treatment inhibits R-EAE. SJL/J mice were immunized with $PLP_{139-151}$ in CFA and injected pertussis toxin i.p. on days 0 and 2. Groups of mice received i.p. injection of GILZ-peptide (500 µg) either on day 0 or on day12/r-GILZ (2 ng)/control peptide (500 µg) in complex with Pep-1 (0.3 µM) or Pep-1 alone or vehicle (PBS) on the day of immunization. (A) The severity of EAE is depicted as the mean score per day, which is the cumulative score for each animal divided by the number of days that animal, was observed. (B) The mean of these values was calculated for each group (n=4 mice/group). GILZ peptide and r-GILZ treated mice had significantly reduced scores. (*, #=p<0.05 as compared with vehicle and control peptide treated mice respectively. No significant differences were observed in the clinical score between vehicle and control peptide-treated mice.

Treatment with GILZ peptide GILZ-P (SEQ ID NO: 6) suppresses R-EAE. The biological potential of GILZ-peptide during antigen priming in vivo was investigated in the relapsing remitting model of EAE. SJL/J mice immunized with $PLP_{139-151}$ were administered vehicle or 500 μg of the GILZ peptide/control peptide/2 ng of r-GILZ/Pep-1 alone on the day of EAE induction or 500 μg of the GILZ peptide 12 days post-induction. The average clinical score per day was significantly lower in mice treated with GILZ-peptide (day 0/day12)/r-GILZ as compared with the control groups (see FIG. 7A). The severity of clinical disease was significantly lower in mice treated with GILZ-peptide on day 0/day12 (mean clinical score: 0.56+/−0.21) and 1.78+/−1.01 respectively) or r-GILZ (mean clinical score 0.17+/−0.14) as compared with the vehicle treated mice (mean clinical score 6.25+/−2.9) or the control peptide or Pep-1 treated mice (mean clinical score 5.7+/−3.4 and 4.7+/−0.8 respectively) (see FIG. 7B). Significantly, while the groups of untreated or mice treated with control peptide or Pep-1 alone exhibited clinical relapse after the initial remission, mice that received GILZ-peptide (day 0/day 12) or r-GILZ exhibited no relapse and continued to be protected for the entire period of observation (see FIG. 7A).

Figure 8:
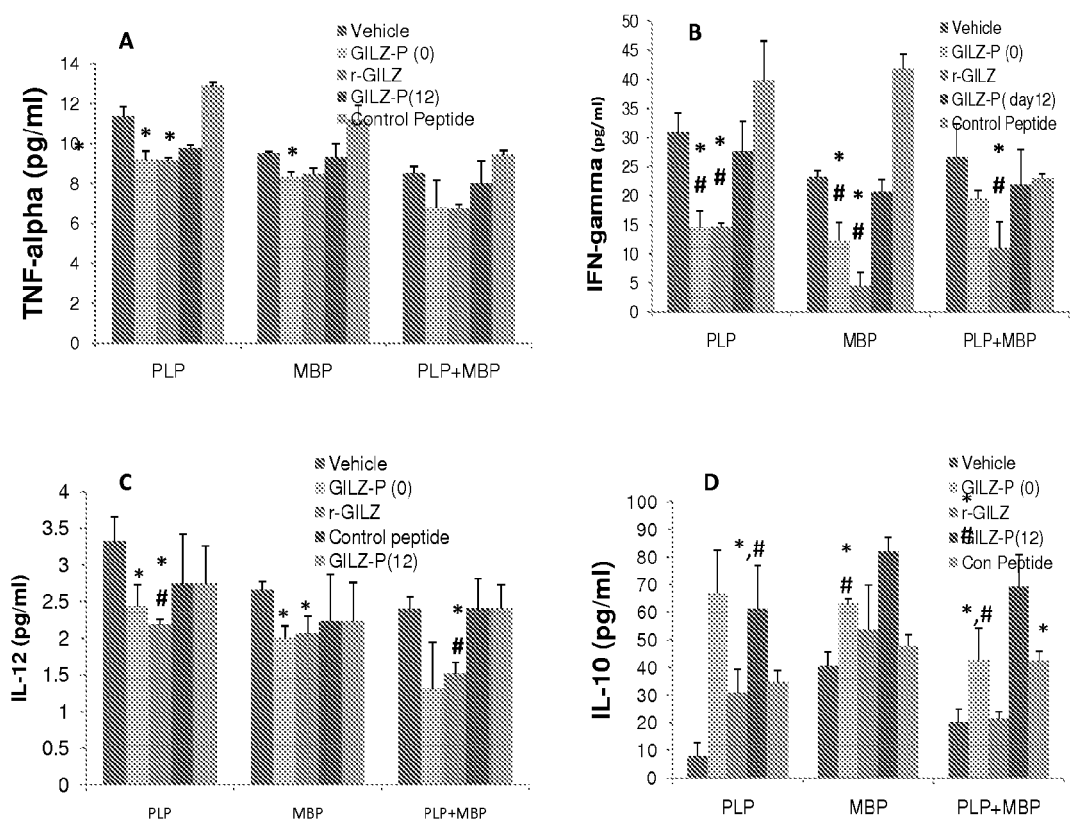
FIG. 8 shows that GILZ peptide treatment reduces proinflammatory cytokine responses in R-EAE. CD4+LNC collected 45 days post-immunization from SJL/J mice induced R-EAE and treated with GILZ peptide (GILZ-P) (day0/day12)/r-GILZ/control peptide/vehicle on the day of immunization were cultured with $PLP_{139-151}$ (40 µg/ml)/$MBP_{87-99}$ 40 µg/ml/both using syngenic irradiated splenocytes as APC. Supernatant collected 48 h later were assessed for TNF-α(A) and IFN-γ (B), IL-12 (C) and IL-10 (D) by ELISA, # represent p<0.05 by ANOVA as compared with vehicle or control peptide treated groups respectively.

GILZ peptide treatment mediates skewing of Th1 to Th2 cytokine response in R-EAE. The effect of the GILZ peptide on T cell cytokine secretion was evaluated. Since the $PLP_{139-151}$ induced R-EAE in SJL/J mice follows a relapsing remitting course secondary to epitope spreading and since the mice treated with GILZ peptide or r-GILZ were protected against disease relapse, the response of T-cells to $PLP_{139-151}$ and to an immunodominant epitope of another encephalitogenic antigen MBP were evaluated. LNC isolated 45 days post-immunization from mice induced with R-EAE and treated with the GILZ peptide (GILZ-P) (SEQ ID NO: 6) (on day 0 or day 12 post-immunization) or r-GILZ protein (SEQ ID NO: 1) secreted significantly reduced Th1 cytokines TNF-α, IFN-γ and IL-12 in response to either $PLP_{139-151}$ or $MBP_{87-99}$ as compared with the cells from vehicle or the control peptide treated mice (see FIGS. 8A, 8B, and 8C). In addition, LNC from R-EAE mice treated with GILZ-peptide/r-GILZ secreted higher IL-10 in response to the $PLP_{139-151}$ and/or $MBP_{87-99}$ as compared with the vehicle or control peptide treated mice (see FIG. 8D). No significant cytokine secretion was observed in cultures stimulated with a previously unexposed antigen, ova.

Taken together these observations suggest that the GILZ peptide protects mice against R-EAE by suppressing Th1 cytokines and skewing towards Th2 responses. An important observation is that the T cell responses not only to the inducing antigen but also to a second central nervous system antigen are suppressed following GILZ peptide administration. This is particularly significant in the context of MS where epitope spreading is associated with new attacks, frequency of relapse, and establishment of chronic inflammation. Hence, therapeutic strategies that not only suppress acute inflammation during an attack but also suppress pathogenesis of relapse are particularly useful in MS.

EXAMPLE 2

Peptides and Reagents

GILZ-$P^{115-137}$ and a control peptide (control-P) of scrambled residues were synthesized as peptide amides and the $PLP_{139-151}$ (HSLGKWLGHPDKF) and $MBP_{89-97}$ (VH-FFKNIVTPRTP) as peptide acids. The amino-terminal of GILZ-P, control-P, and MBP$_{89-97}$ were acetylated. All peptides were 95% pure as confirmed by mass spectrometry. Recombinant human p65 protein (r-p65) and purified r-GILZ with C-terminal DDK and biotinylated anti-DDK antibody were from OriGene Technologies Inc., Rockville, Md. Partial length p65 (p65ΔC14) and anti-p65 mAb were from Active Motif, Carlsbad, Calif. Recombinant mouse GILZ protein and the mouse anti-GILZ mAb (catalog number H00001831-M02) were from Abnova Corporation, Walnut, Calif. The mouse anti-GILZ mAb exhibits cross-reactivity with the human GILZ.

GILZ.p65 Binding

High binding ELISA plates coated with 40 μM r-p65/r-GILZ were probed with cytoplasmic/nuclear extracts, respectively, of CD4+ peripheral blood mononuclear cells stimulated with purified protein derivative (10 units/ml) for 48 h in the presence of dexamethasone (100 μg/ml). Binding of the plate-bound r-p65 with cytoplasmic GILZ and the plate-bound GILZ with nuclear p65 was detected with anti-GILZ mAb or anti-p65 mAb, respectively, followed by trinitrobenzene substrate. For detecting direct interaction of r-GILZ (5-40 μM), captured wells were probed with r-p65 (0.325-40 μM) at 22° C. for 2 h and detected with peroxidase-conjugated anti-GILZ mAb followed by trinitrobenzene substrate. Alternatively plates coated with GILZ-P, control-P (3.9-250 μM), r-GILZ (0.2-1.8 μM) were probed with 40 μM r-p65:DDK/p65ΔC14 and detected with anti-DDK/anti-p65 mAb, respectively. Absorbance at 650 nm was measured between 0 and 300 s with a mixing time of 0.30 s and a 5-s interval between readings.

Treatment of R-EAE

Groups of 8-10-week-old SJL/J female mice induced with EAE were administered intraperitoneally with vehicle/Pep1 (0.3 μM/mouse) mixed with r-GILZ (2 ng/mouse), of GILZ-P, or control-P (500 μg/mouse) in 100 μl of PBS on the day of immunization (day 0). A group of mice received the GILZ-P•Pep-1 complex 12 days post-immunization. rh-GILZ was used to evaluate the effect in R-EAE.

Pep-1-Mediated Delivery

For Pep-1-mediated delivery, complexes of Pep-1•r-GILZ at varying proportions (50:1 μM to 1.25:1 μM or 10:5 μM in PBS) were incubated at room temperature for 30 min. Jurkat T cells were cultured in complete HL-1 medium supplemented with 5% fetal bovine serum, 25 mM HEPES, 2 mM L-glutamine, 50 units/ml of penicillin, 50 mg/ml of streptomycin, and $5 \times 10^5$ M β2-mercaptoethanol in a humidified chamber containing 5% $CO_2$ at 37° C. for 24 h. The cells were then rested for 2 h, washed, and cultured in a 96-well culture plate at $1 \times 10^4$ cells/well in serum-free medium for 60 min. Confluent T cells were then overlaid with the preformed Pep-1•GILZ complexes and incubated at 37° C. for 1 hour. The cells were then extensively washed, permeabilized, and incubated with phycoerythrin-labeled anti-DDK for 30 min at 4° C. Subsequent to washing, the cells were fixed in PBS, 2% paraformaldehyde. The efficiency of r-GILZ intracellular delivery was assessed by measuring the mean fluorescence intensity using FACS Calibur flow cytometer (BD Biosciences).

Proliferation and Cytokine Assays

The LNC/splenocytes were harvested 10 and 45 days post-immunization from R-EAE mice administered vehicle, r-GILZ, control-P, or GILZ-P on days 0 and 12 or left untreated. CD4+ cells isolated by microbead separation were cultured in a transwell system with irradiated syngenic splenocytes as APC in complete HL-1 medium and restimulated with 40 μg/ml of PLP$_{139-151}$, MBP$_{87-99}$ or both, and ova in the presence or absence of dexamethasone ($10^{-7}$-$20^{-7}$ M), r-GILZ (100-200 ng), GILZ-P (125-500 μM), or control-P (500 μM) preincubated with Pep-1 at a 1:20 M ratio for 20 min with Pep-1 alone. Supernatants collected at 24 and 48 h were assessed for specific cytokines using the OptEIA kits (BD Biosciences). Proliferation assays included parallel cultures for 72 h with a final 18-h pulse with [$^3$H]thymidine measured by liquid scintillation counting (Microbeta, Turku, Finland).

NF-κB Assay

5 μg of nuclear extracts isolated from PLP$_{139-151}$ restimulated CD4+ cells from R-EAE mice were incubated in a 96-well plate coated with oligonucleotides containing the NF-κB consensus binding site. The activated NF-κB bound to DNA was detected by anti-p65 antibody followed by a peroxidase-coupled secondary antibody and substrate using the TransAM kit protocol (Active Motif).

Results

Kinetics of GILZ-Peptide-p65 Interaction

Figure 9:
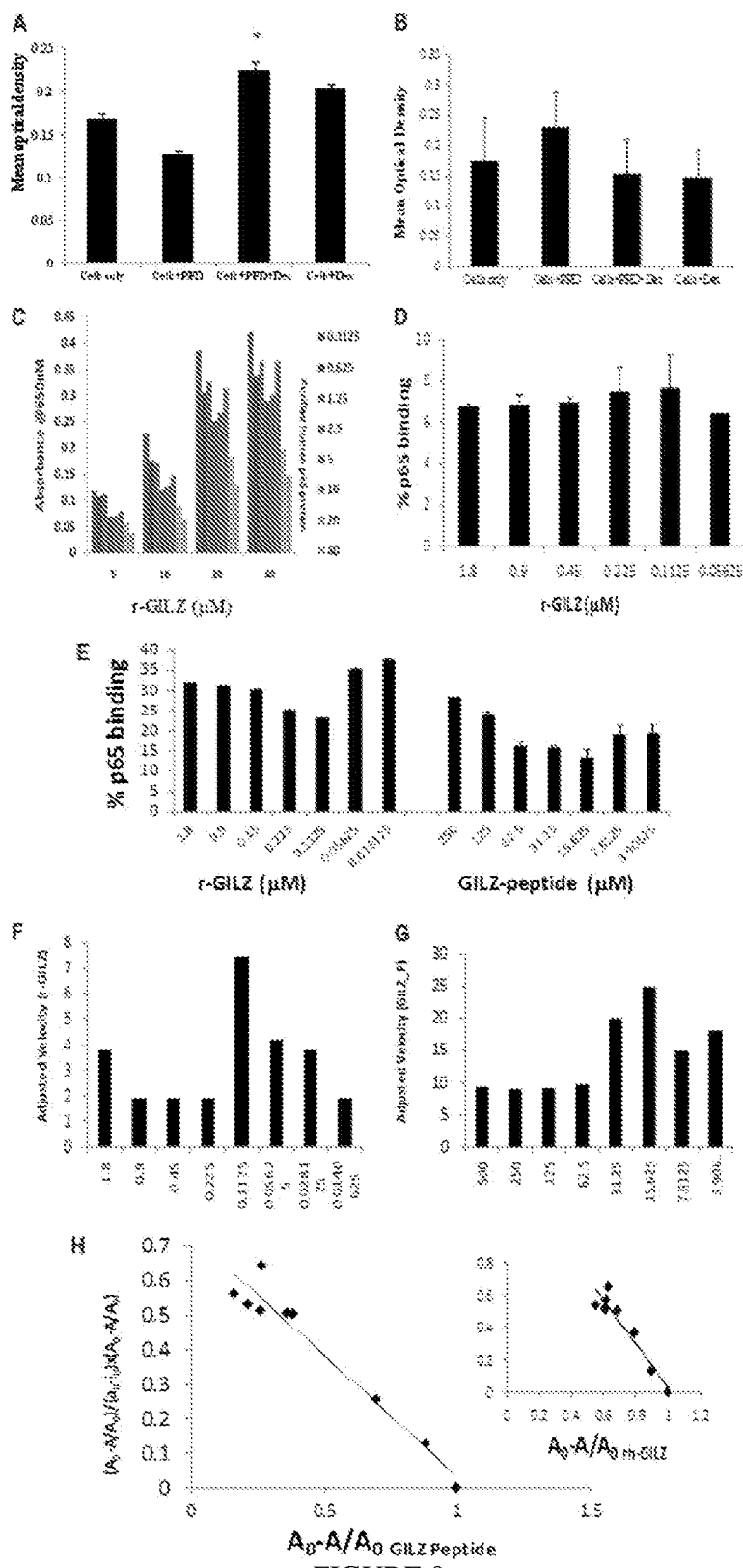
FIG. 9 shows GILZ-p65 binding analysis. CD4+ cells from the peripheral blood mononuclear cells of individuals vaccinated with the BCG vaccine were stimulated with PPD in the presence or absence of dexamethasone. Nuclear and cytoplasmic extracts were obtained from cells harvested after 24 h. Binding between the plate-bound r-p65 and the cytoplasmic GILZ (A) or the plate-bound r-GILZ and nuclear p65 (B) were detected by anti-GILZ (A) or anti-p65 (B) mAb, respectively. *, p<0.05 when compared with cells stimulated with antigen alone. (C) shows wells coated with r-GILZ at increasing concentrations (5-40 µM) were probed with full-length r-p65:DDK at increasing concentrations (0.3125-40 µM) and detected with anti-human GILZ mAb (D). High Bind ELISA plates coated with increasing concentrations of GILZ-P (3.9-250 mM) or r-GILZ (0.2-1.8 µM) were probed with 40 µM r-p65 (E) or r-p65ΔC14 (D) and detected with anti-DDK (E) and anti-p65 mAb (D) followed by trinitrobenzene substrate. Absorbance was read at 605 nm over a period of time between 0 and 300 s with a mixing time of 0.30 s and a 5-s interval between readings prior to stopping. The velocity of r-GILZ-p65 (F) and GILZ-P-p65 (G) reactions was measured as mean optical density/min. Scatchard plot analysis of bound p65 (A0–A/A0) against the ratio of bound p65 to free r-GILZ/GILZ-P (y=(Ao−A/Ao)/(ao−ioxAo−A/Ao)) was used to determine the dissociation constant for the interaction between r-GILZ-p65 and GILZ-P and p65 (H).

The interaction between GILZ and p65 proteins by modified cellular ELISA was investigated. Treatment with dexamethasone increases GILZ expression and suppresses p65 translocation in activated T cells. Hence, the nuclear or cytoplasmic protein fractions derived from the CD4+ T cells stimulated with recall antigen in the presence of dexamethasone were assessed for binding plate-bound r-GILZ or r-p65, respectively. Although the absorbance was significantly increased in the r-p65-coated wells probed with the cytoplasmic fraction of dexamethasone-treated activated CD4+ T cells (see FIG. 9A), it was significantly decreased in r-GILZ-coated wells probed with the nuclear fraction of CD4+ T cells activated in the presence of dexamethasone as compared with untreated cells (see FIG. 9B). Reduced p65 in the nuclear fractions of cells treated with dexamethasone alone is consistent with its ability to inhibit NF-κB translocation in unstimulated cells (see FIG. 9B).

To detect direct interaction, the ability of r-p65 to inhibit the binding of anti-GILZ mAb with the plate-bound r-GILZ was assessed. The GILZ anti-GILZ complex formation was inhibited by r-p65 in a dose-dependent manner (see FIG. 9C). To determine the kinetics of interaction between r-GILZ/GILZ-P and the p65, plate-bound r-GILZ, GILZ-P, and control-P at varying concentrations was probed with full-length r-p65-DDK. The percent of p65 binding decreased with decreasing concentrations of r-GILZ/GILZ-P (see FIG. 9E). The adjusted velocity of the interaction between r-p65 and r-GILZ (7.5/s) or GILZ-P (25/s) was observed at 1:4 molar concentrations (see FIGS. 9F and 9G). A plot of the change in absorbance with time showed that maximum absorbance was reached at a later time point in the binding of r-GILZ (210 s) than of GILZ-P (38 s) with r-p65 suggesting a slower association rate and hence weaker strength for the former interaction as compared with the latter (data not shown). Scatchard plot and linear regression analysis suggested that the dissociation constant, $K_D$, for the interaction between r-GILZ or GILZ-P and r-p65 were $5.91 \pm 2.4 \times 10^{-7}$ M (see FIG. 9H) and $1.12 \pm 0.25 \times 10^{-6}$ M (see FIG. 9H), respectively. Absorbance over background was not observed when plate-bound r-GILZ/GILZ-P was probed with p65ΔC14 and detected with anti-p65 mAb (see FIG. 9E, suggesting that the GILZ-P potentially interacts selectively with the p65-TAD. Significant absorbance was not observed in wells coated with control-P and probed with r-p65/p65ΔC14 (see FIG. 9D).

Pep-1-Mediated Intracellular Delivery of r-GILZ in T Cells

Figure 10:
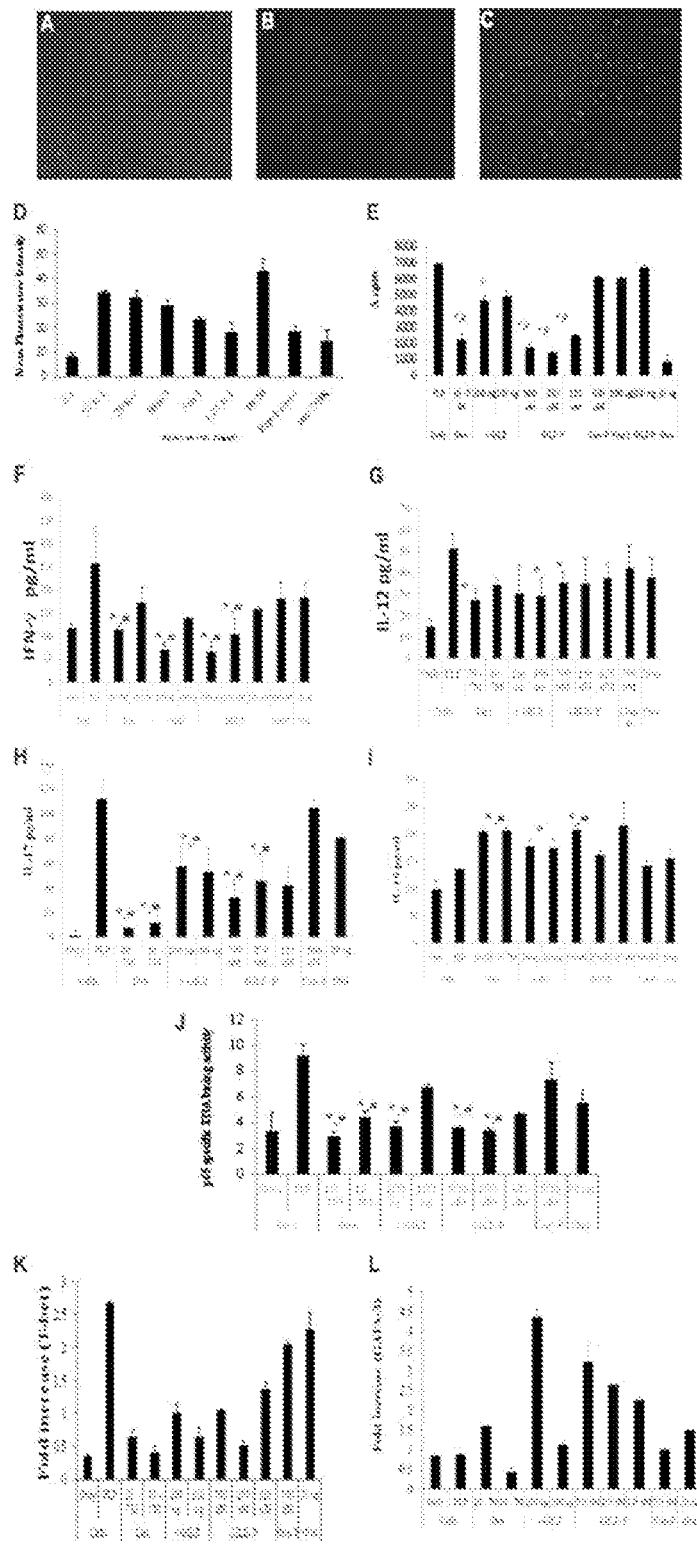
FIG. 10 (A)-(D) shows intracellular delivery of r-GILZ by Pep-1:Jurkat T cells in serum-free HL-1 medium were overlaid with a pre-formed complex of r-GILZ (DDK tag) and Pep-1 at varying concentrations and incubated in a humidified chamber for 1 h at 37° C. Intracellular delivery of r-GILZ was detected using phosphatidylethanolamine-labeled anti-DDK mAb in permeabilized cells and measured by FACS Calibur. Representative images of cells incubated with (A) r-GILZ alone, (C) 20:1 ratio of Pep-1 to r-GILZ, and (B) pep-1 alone are shown. The delivery efficiency was assessed by mean fluorescence intensity (D). Data are average of two different experiments±S.E. (E)-(L) shows treatment with GILZ-peptide suppress T cell responses. CD4+ splenocytes (5×10⁵ cells/well) isolated from antigen-primed SJL mice were co-cultured with irradiated syngenic splenocytes as APC and restimulated with PLP139-151 (40 µg/ml) for a total of 72 h (including an 18-h pulse with [3H]thymidine) in the presence of dexamethasone (20-7/$10^{-7}$ M), r-GILZ (100 and 200 ng), GILZ-P (125-500 µM), and control peptide (C-P)(500 µM) as shown. (E) shows data represent mean Δcpm (cpm of the antigen-stimulated cells—cpm of cells only) ±S.D. from three different experiments. (F)-(I) show supernatants collected at 48 h were assessed for IFN-γ (F), IL-12 (G), IL-17 (H), and IL-10 (I) by ELISA. Data are presented as mean±S.D. (J) shows in separate experiments, draining LNC cultured similarly were harvested at the end of 24 h. Five micrograms of nuclear extracts were tested for binding of the activated p65 NF-κB subunit to an NF-κB consensus sequence using the TransAM NF-κB ELISA kit. The p65 DNA binding activity was calculated as the ratio of absorbance from PLP139-151-stimulated cells to that of unstimulated cells. Values are the average±S.D. performed 3 times in duplicate. (K)-(L) show real time PCR for T-bet (K) and GATA-3 (L) was performed using 50 ng of cDNA isolated from CD4+LNC of R-EAE mice re-stimulated in vitro with PLP139-151 under the indicated conditions. Treatment with dexamethasone, r-GILZ, and GILZ-peptide down-regulated T-bet (K) and up-regulated GATA-3 (L) expression in activated CD4+ T cells. * and #, p<0.05 as compared with the cells treated with PLP139-151 alone or cells stimulated in the presence of control-P, respectively.

For an effective intracellular concentration, r-GILZ/GILZ-P/control-P were mixed with an amphipathic chariot peptide, Pep-1, which rapidly associates through hydrophobic noncovalent interactions and forms stable nanoparticle complexes in solution independent of cargo sequence or size (see FIG. 10A-10C). The efficiency of Pep-1 to deliver biological molecules was investigated by incubating Jurkat T cells with preformed complexes of Pep-1 and r-GILZ at varying concentrations. Intracellular delivery was seen in cells incubated with a r-GILZ•Pep-1 complex but not in cells incubated with r-GILZ/Pep-1 alone (see FIG. 10A-10C). The delivery was most efficient in cells incubated with Pep-1 and r-GILZ at the molar ratio of 50/20:1 as evidenced by the higher mean fluorescence intensity (see FIG. 10D). The delivery efficiency decreased with decreasing concentrations of Pep-1 (see FIG. 10D). The mean fluorescence intensity was equivalent in untreated cells and cells overlaid with r-GILZ/Pep-1 alone (see FIG. 10D). Pep-1 has been effectively used for intracellular delivery of different cargos; including peptide inhibitors of protein kinases, apoptotic protein, and small interfering RNA.

Effect of GILZ-Peptide on T Cell Responses

To investigate the ability of GILZ-peptide to interfere with the GILZ-p65 interactions, in vitro T cell proliferation assays were performed. A significantly decreased proliferative response (mean Δcpm) was observed in CD4+ LNC isolated from R-EAE mice and re-stimulated in vitro with $PLP_{139-151}$ in the presence of dexamethasone/r-GILZ/GILZ-P with maximum inhibition in cultures treated with 250 μM GILZ-P (1404±106). No significant inhibition was observed in cultures treated with control-P (6079±70), Pep-1 alone (6022±87), or GILZ-P alone (6663±173) (see FIG. 10E). $PLP_{139-151}$ primed CD4+ cells did not exhibit a significant response to an irrelevant antigen, ova (418±24).

The GILZ-P-mediated reduction in proliferation was investigated for its association with the modulation of cytokine response and p65 transactivation. CD4+ LNC from $PLP_{139-151}$-primed mice re-stimulated in vitro in the presence of dexamethasone/GILZ-P/r-GILZ secreted significantly lower pro-inflammatory IFN-γ (see FIG. 10F), IL-12 (see FIG. 10G), and IL-17 (see FIG. 10H) but elevated anti-inflammatory IL-10 cytokine (see FIG. 10I) as compared with untreated/control-P-treated cells. Furthermore, in vivo primed CD4+ LNC re-stimulated with $PLP_{139-151}$ in the presence of dexamethasone/r-GILZ/GILZ-P exhibited significantly decreased T-bet mRNA (see FIG. 10I), the canonical Th1 transcription factor, and elevated GATA-3 (see FIG. 10L), the Th2 transcription factor, as compared with unstimulated/control-P-treated cells. Importantly, significantly decreased p65-specific DNA binding activity was observed in nuclear extracts of CD4+ LNC-restimulated with $PLP_{139-151}$ in the presence of dexamethasone/r-GILZ/GILZ-P as compared with untreated or control-P-treated cells (see FIG. 10J).

GILZ-P Protects Against R-EAE

The biological potential of GILZ-P during antigen priming in vivo was investigated in R-EAE. On day 0 groups of SJL/J mice were induced by R-EAE and administered a single intraperitoneal injection of PBS or a complex of Pep-1 and r-GILZ/GILZ-P/control-P. Separate groups of mice received a single dose of Pep-1•GILZ-P on day 12 post-immunization. The average clinical score per day was significantly lower in mice treated with GILZ-P (day 0/day12), r-GILZ as compared with the control groups (see FIGS. 11A and 11B). The severity of clinical disease as suggested by the mean total clinical score was significantly lower in mice treated with GILZ-P (day 0, 2.25±0.72; day 12, 15.75±4.85) or r-GILZ (7.13±2.8) as compared with vehicle (28.5±5.57) or control-P (33±7.5)-treated mice. Significantly, whereas the vehicle or control-P-treated mice exhibited clinical relapse after initial remission, the mice that received GILZ-P/r-GILZ exhibited minimal relapse and continued to be protected for the entire period of observation (see FIG. 11A).

GILZ-Peptide Suppresses T Cell Responses in R-EAE

To determine whether the protection mediated by GILZ-P is due to modulation of T cell responses, the functional responses of CD4+ splenocytes from R-EAE mice treated with PBS/r-GILZ/GILZ-P/control-P were assessed. Proliferative responses (mean Δcpm) to $PLP_{139-151}$ were significantly decreased in CD4+ splenocytes from mice treated with the r-GILZ (16,880±264), GILZ-P (5,733±208, day 0) as compared with that from vehicle (38,657±533) or control-P (32,460±940)-treated mice (see FIG. 11C). The average proliferative response of unstimulated CD4+ splenocytes for vehicle, r-GILZ, GILZ-P (day 0), GILZ-P (day 12), and control-P-treated groups of mice was 2,695±608, 2,037±603, 2,376±602, 1,823±532, and 2,645±425, respectively. No significant difference was observed in the proliferative responses of splenocytes to ovalbumin between the different treatment groups (see FIG. 11C).

The effect of in vivo GILZ treatment in inflammatory cytokine responses was investigated. Upon re-stimulation with $PLP_{139-151}$ the secretion of Th1 cytokines IL-12 and IFN-γ was significantly reduced in CD4+ splenocytes from mice treated on day 0 with r-GILZ (22.5±01.05 and 100.5±6.8 pg/ml, respectively) or GILZ-P (12.7±0.47 and 96.5±7.1 pg/ml, respectively) than from vehicle (53.3±5.2 and 132.9±7.6 pg/ml, respectively) or control-P (54±4.2 and 111.8±5.6 pg/ml, respectively)-treated mice (see FIGS. 11D and 11E). Although IL-12 was significantly lower in CD4+ cells from mice treated with GILZ-P 12 days post-immunization, the reduction in IFN-γ was not significant as compared with that from control groups of mice. The IL-17 secretion by $PLP_{139-151}$ re-stimulated CD4+ cells from mice treated on day 0 with r-GILZ (10.66±0.2 pg/ml) or GILZ-P (10.85±0.3 pg/ml) was significantly decreased as compared with cells from vehicle (12±0.7 pg/ml) or control-P (11.95±0.11 pg/ml)-treated mice (see FIG. 11F). In contrast, the anti-inflammatory IL-10 secretion was significantly increased in the $PLP_{139-151}$-stimulated cultures of CD4+LNC from mice treated on day 0 with GILZ-P (2316±52.9 pg/ml) as compared with that from vehicle (1456±83.8 pg/ml) or control-P (1488±22.9 pg/ml)-treated mice (see FIG. 11G).

Figure 11:
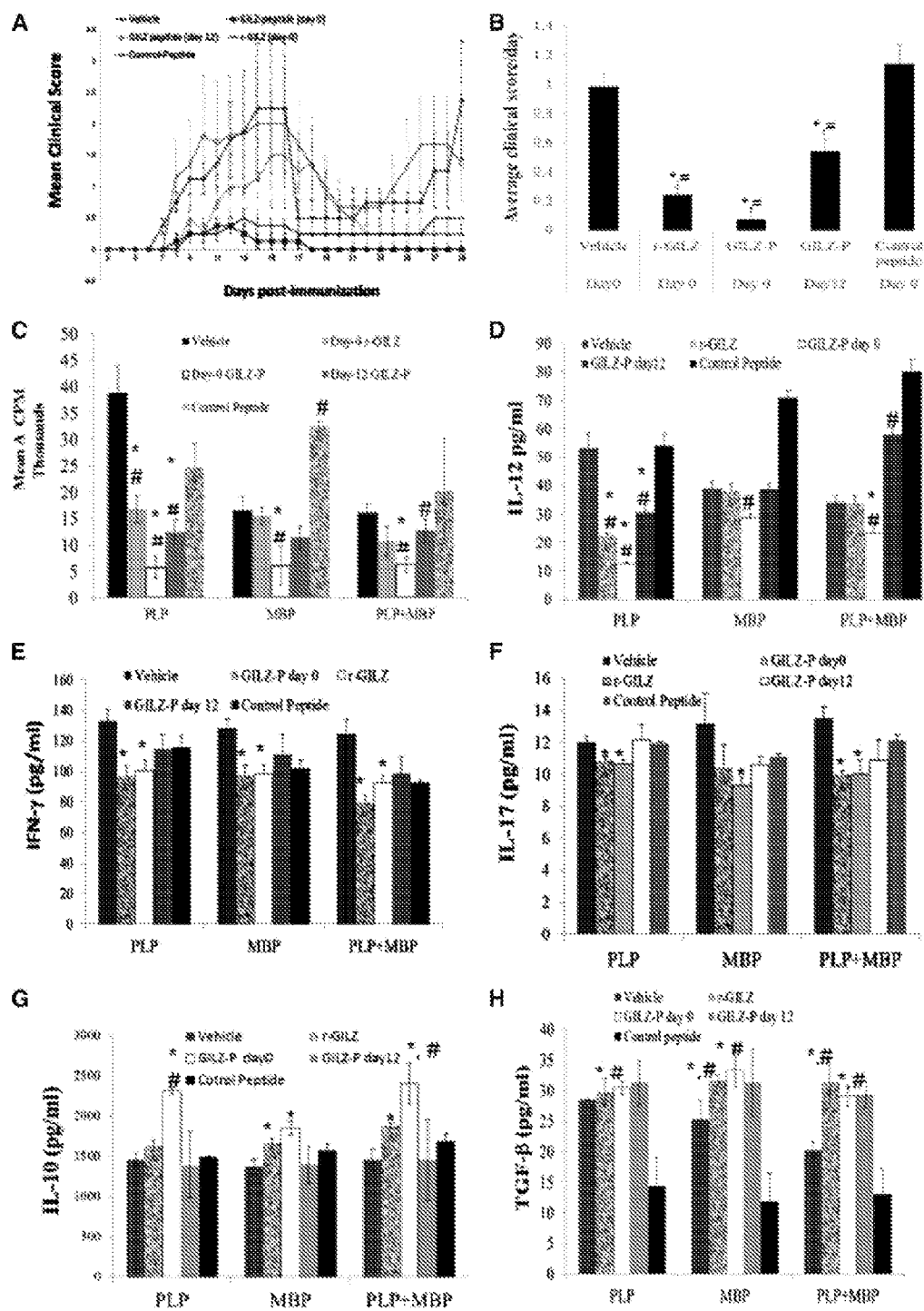
FIG. 11 shows GILZ-peptide treatment inhibits R-EAE. SJL/J mice induced with R-EAE were administered intraperitoneally GILZ-peptide (500 µg) either on day 0 or 12 for r-GILZ (2 ng) and control peptide (500 µg) in complex with Pep-1 (0.3 µM) or Pep-1 alone, or vehicle (PBS) on the day of immunization. (A) shows the mean clinical score per day per group. (B) shows the severity of EAE is depicted as the mean score per day, which is the cumulative score for each animal divided by the number of days that animal was observed. Data represent average±S.D. from two experiments (n=9/group). (C)-(H) show GILZ-peptide treatment suppresses Th1 cytokines in R-EAE. CD4+ splenocytes isolated 45 days post-immunization from the draining lymph nodes of SJL/J mice induced with R-EAE and treated with GILZ-peptide (500 µg) either on day 0 or 12 for r-GILZ, control peptide, or vehicle (PBS) were restimulated in vitro with PLP139-151 (40 µg/ml), MBP87-99 (40 µg/ml), or both using syngenic irradiated splenocytes as APC for a total of 72 h (including an 18-h pulse with [3H]thymidine). C, proliferative responses of CD4+ splenocytes are plotted as Δcpm±S.E. #, p<0.05 as compared with the responses of cells from vehicle-treated mice. Supernatant collected at 48 h from separate CD4+ splenocyte cultures were assessed for (D) IL-12, (E) IFN-γ, (F) IL-17, (G) IL-10, and (H) TGF-β by ELISA. * and # represent p<0.05 as compared with vehicle or control peptide-treated groups, respectively.

Because R-EAE is a relapsing disease secondary to epitope spreading (32), the effect of GILZ-P on T cell cytokine responses to a second common encephalitogenic epitope in SJL/J EAE, the $MBP_{89-97}$ was evaluated The $MBP_{87-99}$-stimulated CD4+ splenocytes from mice treated on day 0 with GILZ-P secreted significantly lower IL-12 (28.4±1.6 pg/ml), IFN-γ (97.4±6.9 pg/ml), and IL-17 (10.43±0.4 pg/ml) as compared with vehicle/control-P treated mice (see FIG. 11D-11F). Importantly, significantly elevated IL-10 cytokine was secreted by CD4+ splenocytes from mice treated on day 0 with r-GILZ (1667±63.7 pg/ml) or GILZ-P (1850.8±90 pg/ml) in response to $MBP_{87-99}$ (see FIG. 11G). Furthermore, $MBP_{87-99}$ but not $PLP_{139-151}$ stimulation significantly increased TGF-β secretion by CD4+ splenocytes from mice treated on day 0 with GILZ-P (33.31±4 pg/ml) or r-GILZ (31.7±0.8 pg/ml) as compared with vehicle (25.3±2.9 pg/ml) or control-P (11.8±4.7 pg/ml)-treated mice (see FIG. 11H). No significant difference was observed in the response of the CD4+LNC from the different groups of mice to ova, a control antigen.

GILZ-Peptide Increases Expression of Regulatory Molecules in T Cells in R-EAE

Figure 12:
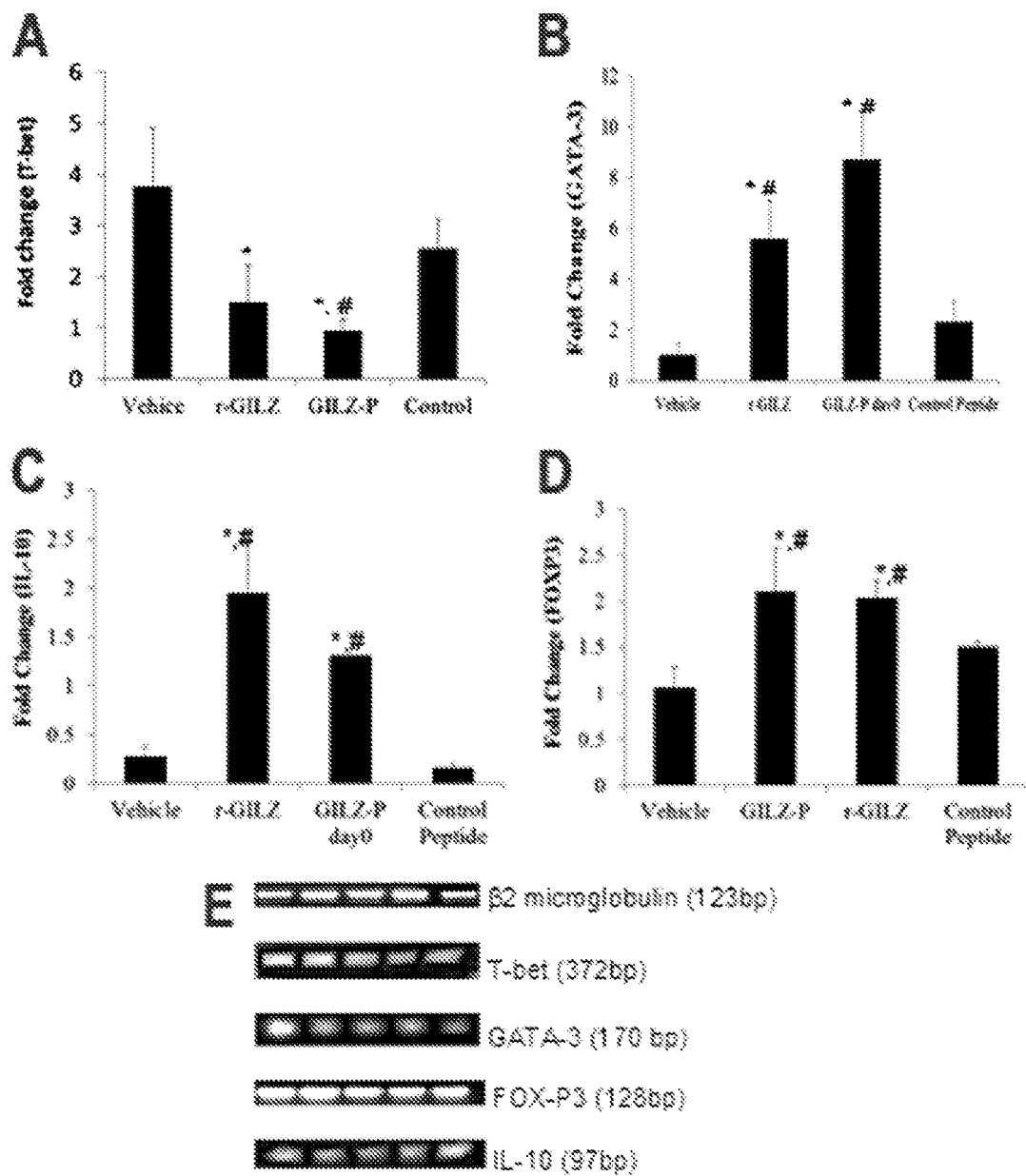
FIG. 12 shows GILZ-peptide treatment suppresses Th1 and enhances Th2 transcription factors in R-EAE. CD4+ LNC isolated 45 days post-immunization from the draining lymph nodes of SJL/J mice induced with R-EAE and treated with GILZ-peptide (500 µg) either on day 0 with vehicle, r-GILZ, control-P, or vehicle (PBS) or on day 12 with GILZ-P (n=9/group) were restimulated in vitro with PLP139-151 (40 mg/ml) using syngenic irradiated splenocytes as APC in transwell systems. 50 ng of cDNA from CD4+LNC were used for quantitative measurement of message for (A) T-bet, (B) GATA-3, (C) IL-10, and (D) FoxP3 by quantitative RT-PCR. (E), gel electrophoresis of representative products. * and # represent p<0.05 by analysis of variance as compared with vehicle or control peptide-treated group, respectively.

The ability of GILZ-peptide to facilitate Th1 to Th2 skewing was evaluated in vivo by modulating specific transcription factors, T-bet and GATA-3, respectively. RT-PCR showed that the CD4+ LNC from mice induced EAE and treated on day 0 with vehicle/r-GILZ/GILZ-P/control-P exhibited significantly lower T-bet but elevated GATA-3 mRNA following re-stimulation with $PLP_{139-151}$ (see FIGS. 12A and 12B). GILZ has been shown to induce IL-10 secretion and promote regulatory T cell differentiation. Accumulation of FOXP3+ IL-10 secreting regulatory T cells in the CNS has been associated with disease recovery in EAE. The CD4+ T cells from mice treated on day 0 with r-GILZ/GILZ-P exhibited significantly higher expressions of IL-10 and FoxP3 mRNA as compared with that from vehicle/control-P-treated mice (see FIGS. 12C and 12D).

EXAMPLE 3

Circular Dichroism

CD measurements can be recorded on a JASCO model, J-710 spectropolarimeter, (Jasco Inc, Easton, Md.) as described previously. The samples can be prepared by dissolving lyophilized GILZ peptide or control peptides at 100 μM concentration in citrate buffer (1 mM sodium citrate, 1 mM sodium borate, 1 mM sodium phosphate, 15 mM NaCl) with pH adjusted at 7.0. CD spectra can be collected using a 1 cm path-length quartz cuvette at 50° C. or 90° C. in the 190- to 270-nm wavelength range with a 0.5 nm resolution and a scan rate of 200 nm/min. Reported spectra can represent the unsmoothed averages of 30 scans. Each spectrum can be measured three times with individually prepared solutions. Raw CD signals (in millidegrees) can be converted to mean residue molar ellipticity (θ) in deg cm²/dmol using the formula [θ] MRW 5 [θ]obs/101cn, where θ obs is the observed ellipticity, 1 is the pathlength in centimeters, c is the molar concentration of peptide, and n is the number of residues in the peptide. To determine 0% $PP_{II}$ helical content CD spectra can be recorded with GILZ-peptide dissolved in 5M $CaCl_2$.

Figure 13:
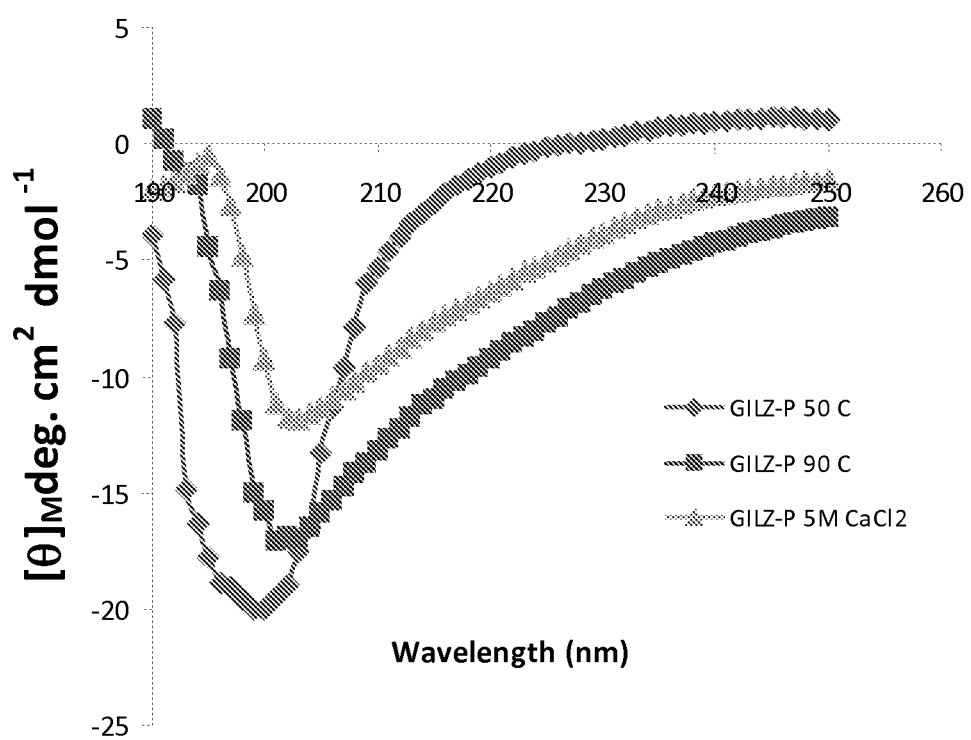
FIG. 13 shows the CD spectrum of GILZ-P at various temperatures and in 5M $CaCl_2$.

The CD spectrum of GILZ-P demonstrates a large minimum at 200 nm (θ=−20.03×10³ deg·cm²/dmol) and a slight maximum at 238 nm (θ=1.12×10³ deg cm² dmol⁻¹) at 50° C. These observations are consistent with the CD spectrum of polypeptide sequences reported to prefer a $PP_{II}$ helical structure. When the temperature was raised to 90° C., there is a decrease in the mean residue molar ellipticity and a shift to the right (θ=−11.37×10³ deg cm²/dmol @ 204 nM) (see FIG. 13). Similar variation with increasing temperature has been observed in proline-rich peptides, due to a transition from the $PP_{II}$ helical structure to random coil conformation. The CD spectrum of GILZ-P in 5M $CaCl_2$ exhibits a dramatic decrease in the intensity of the mean residue ellipticity minimum at 205 nM (θ=−8.84×10³ deg cm²/dmol) suggesting complete disruption of the helical structure (see FIG. 13). The CD spectrum of CP-1 and CP-2 shows a weak minimum of θ=−4.5×10¹ deg cm²/dmol and θ=−3.5×10¹ deg cm²/dmol) at 194 nm respectively (see FIG. 13).

Experimental Procedures

Figure 14A:
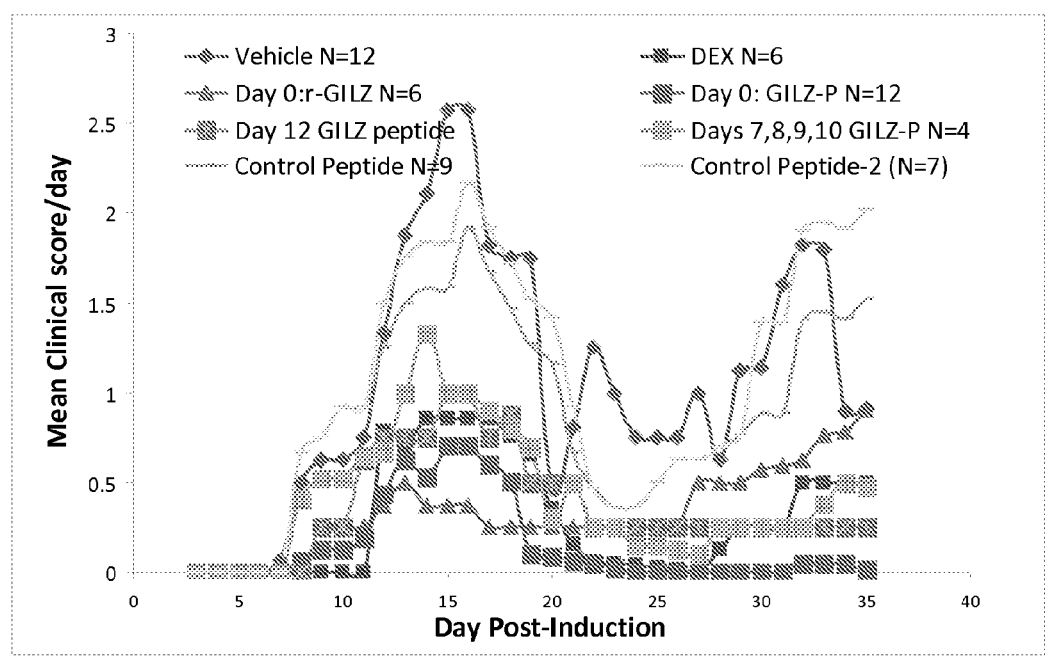
FIG. 14 shows GILZ-peptide treatment inhibits R-EAE. (A) shows the mean clinical score per day per group. (B) shows the severity of EAE is depicted as the mean score per day, which is the cumulative score for each animal divided by the number of days that animal was observed.
Figure 14B:
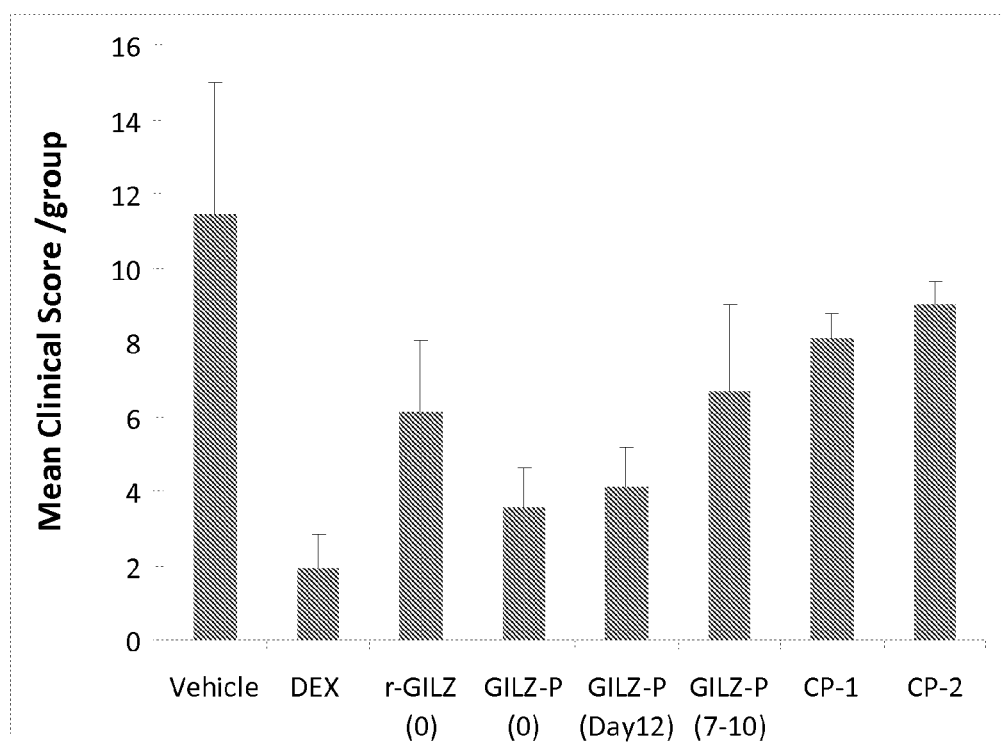

The effect of GILZ peptide/mimics treatment in ongoing disease can be evaluated. 8-10 wks old SJL/J mice (The Jackson Laboratory, Bar Harbor, Me.) can be immunized with a solution of proteolipin protein peptid ($PLP_{139-151}$) (100 μg/mouse) in phosphate buffered saline emulsified with equal volume of complete Freund's adjuvant 200 μg of *Mycobacterium tuberculosis* H37RA (Difco Laboratories). Each mouse can receive 25 ul given subcutaneously in the lateral flanks. For treatment, mice can be administered intra-peritoneally vehicle/dexamethasone (dex:0.3 mg/kg)/(500 μg) of GILZ-P/CP-1/CP-2 mixed with carrier peptide Pep1 (0.304/mouse) in 100 μl PBS on the day of immunization. A group of mice can receive GILZ-P (100 μg/day): Pep-1 complex on days 7, 8, 9 and 10 post-induction. CP-1 is a control peptide for the GILZ mimic structure and CP-2 is a control peptide for the GILZ mimic amino acid sequence. Mice can be monitored daily and the clinical score will be recorded. The mean clinical score per day per group is shown in FIG. 14(A). The severity of EAE is depicted in FIG. 14(B) as the mean score per day, which is the cumulative score for each animal divided by the number of days that animals were observed.

Serum Cytokine Assays

Peripheral blood from R-EAE mice administered vehicle/dexamethasone/r-GILZ (2 ng/mouse)/(500 μg) of GILZ-P/CP-1/CP-2/GILZ-P (100 μg) on days 7, 8, 9 and 10 can be collected from tail vein on day 4 and day 7 post-disease induction. Serum cytokines can be assessed using the OptEIA kits (BD Biosciences, CA).

In Vitro Proliferation and Cytokine Assay

Figure 15A:
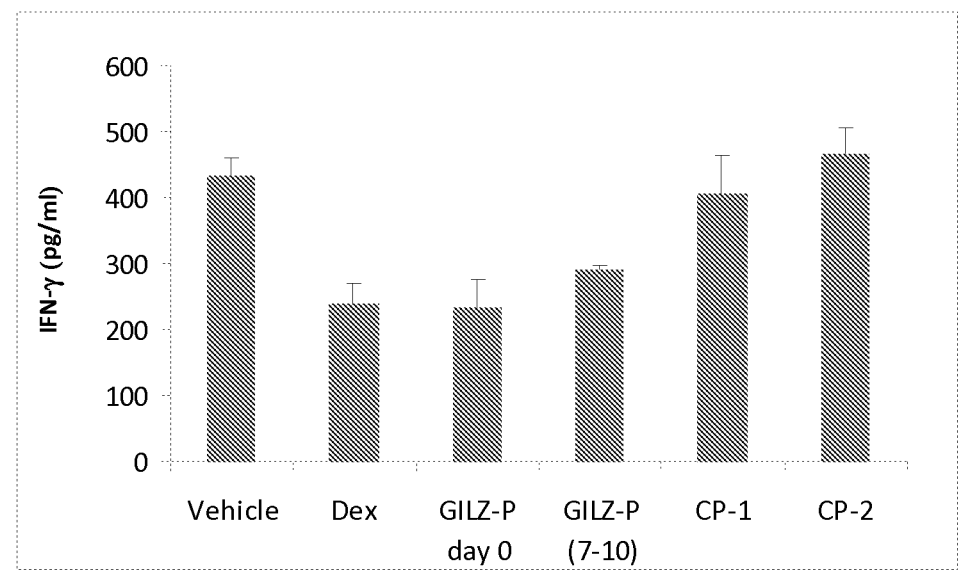
FIG. 15 shows assays of specific cytokines ((A) IFN-γ, (B) TNF-α, and (C) IL-17) assayed from supernatants collected at 48 hours.
Figure 15B:
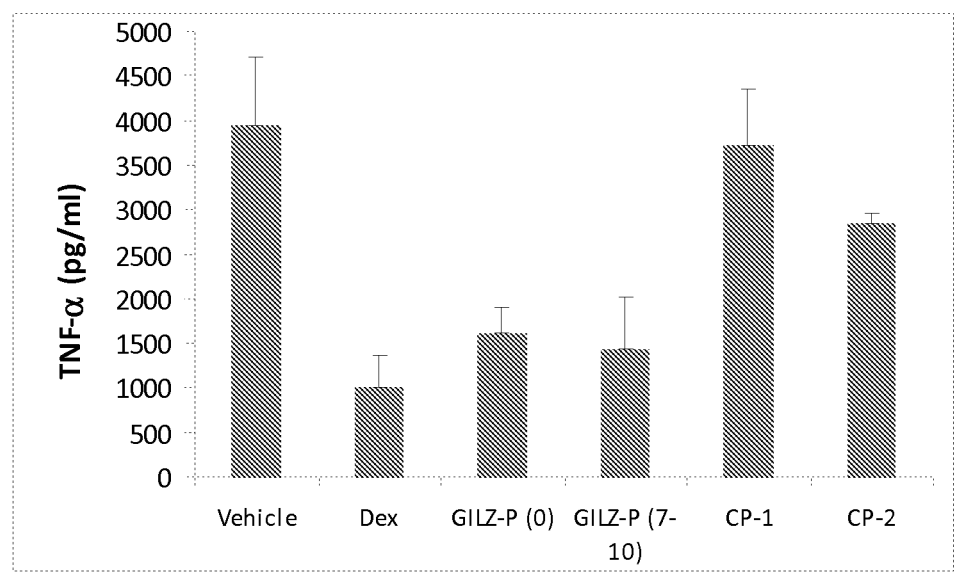
Figure 15C:
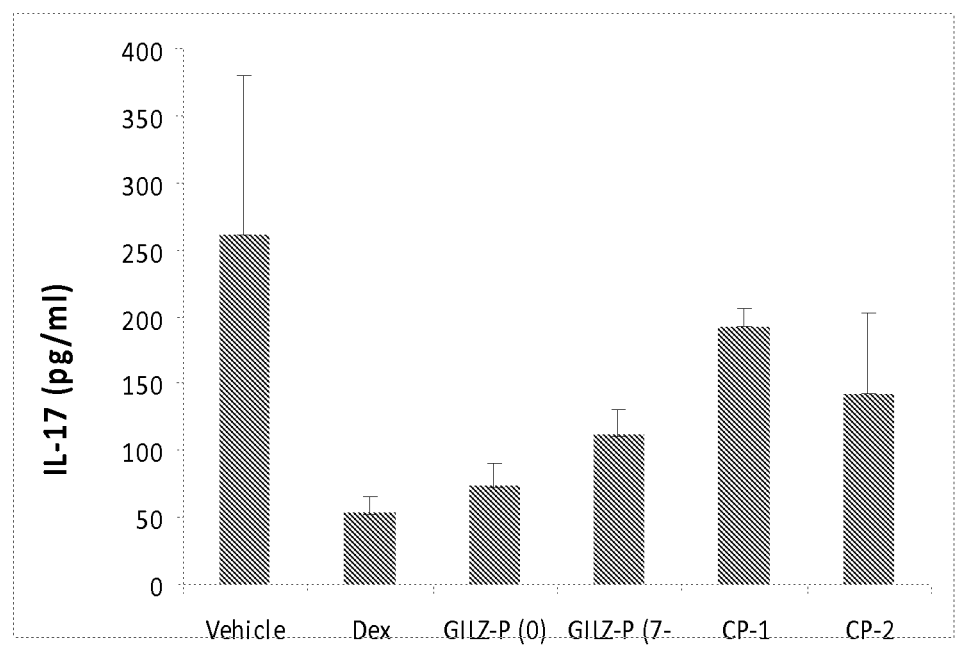

Draining lymph nodes and spleen can be harvested 35 days pot-immunization from R-EAE mice administered vehicle/dexamethasone/(500 μg) of GILZ-P/CP-1/CP-2/GILZ-P (100 μg) on days 7, 8, 9 and 10. Single cell suspensions of lymph node cells can be cultured in complete RPMI in the presence or absence of 40 μg/ml of $PLP_{139-151}$/$MBP_{87-99}$/both/ova. Supernatants collected at 48 hours can be assessed for specific cytokines FIGS. 15(A), 15(B), and 15(C) show the assayed results for IFN-γ, TNF-α, and IL-17, respectively.

All of the patents, patent applications, patent application publications and other publications recited herein are hereby incorporated by reference as if set forth in their entirety.

While the invention has been illustrated and described in detail in the foregoing description, such an illustration and description is to be considered as exemplary and not restrictive in character, it being understood that only the illustrative embodiments have been shown and described and that all changes and modifications that come within the spirit of the invention are described and included as further embodiments.

What is claimed is:

1. A pharmaceutical composition comprising a polypeptide from 6 to 35 amino acid residues, the polypeptide comprising 1 to 3 tetrapeptides having the sequence of PXXP, wherein
    P is proline; and
    X is any amino acid, and
    wherein the polypeptide comprises the amino acid sequence of CLSPEEPAPESPQVPEAPGGSAV (SEQ ID NO: 6),
    and wherein the pharmaceutical composition further comprises a cell penetrating peptide, wherein the polypeptide and the cell penetrating peptide form a complex.

2. The pharmaceutical composition of claim 1, wherein at least one tetrapeptide comprises the amino acid sequence of SEQ ID NO: 3.

3. The pharmaceutical composition of claim 1, wherein at least one tetrapeptide comprises the amino acid sequence of SEQ ID NO: 4.

4. The pharmaceutical composition of claim 1, wherein at least one tetrapeptide comprises the amino acid sequence of SEQ ID NO: 5.

5. The pharmaceutical composition of claim 1, wherein the polypeptide comprises a polyproline helical conformation.

6. The pharmaceutical composition of claim 1, wherein the cell penetrating peptide is Pep-1.

7. The pharmaceutical composition of claim 1, wherein the composition provides a Th-2 bias in the Th-1/Th-2 balance.

8. A pharmaceutical formulation comprising the pharmaceutical composition of claim 1.

9. The pharmaceutical formulation of claim 8 further comprising a pharmaceutically acceptable carrier.

10. A lyophilisate or powder of the pharmaceutical formulation of claim 8.

* * * * *

SEQUENCE LISTING

```
<160> NUMBER OF SEQ ID NOS: 7

<210> SEQ ID NO 1
<211> LENGTH: 134
<212> TYPE: PRT
<213> ORGANISM: Artificial Sequence
<220> FEATURE:
<223> OTHER INFORMATION: Synthetic peptide

<400> SEQUENCE: 1

Met Asn Thr Glu Met Tyr Gln Thr Pro Met Glu Val Ala Val Tyr Gln
1               5                   10                  15
```

-continued

```
Leu His Asn Phe Ser Ile Ser Phe Phe Ser Ser Leu Leu Gly Gly Asp
            20                  25                  30

Val Val Ser Val Lys Leu Asp Asn Ser Ala Ser Gly Ala Ser Val Val
        35                  40                  45

Ala Ile Asp Asn Lys Ile Glu Gln Ala Met Asp Leu Val Lys Asn His
50                  55                  60

Leu Met Tyr Ala Val Arg Glu Val Glu Ile Leu Lys Glu Gln Ile
65                  70                  75                  80

Arg Glu Leu Val Glu Lys Asn Ser Gln Leu Glu Arg Glu Asn Thr Leu
                85                  90                  95

Leu Lys Thr Leu Ala Ser Pro Glu Gln Leu Glu Lys Phe Gln Ser Cys
            100                 105                 110

Leu Ser Pro Glu Glu Pro Ala Pro Glu Ser Pro Gln Val Pro Glu Ala
            115                 120                 125

Pro Gly Gly Ser Ala Val
        130
```

<210> SEQ ID NO 2
<211> LENGTH: 35
<212> TYPE: PRT
<213> ORGANISM: Artificial Sequence
<220> FEATURE:
<223> OTHER INFORMATION: Synthetic peptide

<400> SEQUENCE: 2

```
Leu Ala Ser Pro Glu Gln Leu Glu Lys Phe Gln Ser Cys Leu Ser Pro
1               5                   10                  15

Glu Glu Pro Ala Pro Glu Ser Pro Gln Val Pro Glu Ala Pro Gly Gly
            20                  25                  30

Ser Ala Val
        35
```

<210> SEQ ID NO 3
<211> LENGTH: 4
<212> TYPE: PRT
<213> ORGANISM: Artificial Sequence
<220> FEATURE:
<223> OTHER INFORMATION: Synthetic peptide

<400> SEQUENCE: 3

```
Pro Glu Glu Pro
1
```

<210> SEQ ID NO 4
<211> LENGTH: 4
<212> TYPE: PRT
<213> ORGANISM: Artificial Sequence
<220> FEATURE:
<223> OTHER INFORMATION: Synthetic peptide

<400> SEQUENCE: 4

```
Pro Glu Ser Pro
1
```

<210> SEQ ID NO 5
<211> LENGTH: 4
<212> TYPE: PRT
<213> ORGANISM: Artificial Sequence
<220> FEATURE:
<223> OTHER INFORMATION: Synthetic peptide

<400> SEQUENCE: 5

```
Pro Glu Ala Pro
1

<210> SEQ ID NO 6
<211> LENGTH: 23
<212> TYPE: PRT
<213> ORGANISM: Artificial Sequence
<220> FEATURE:
<223> OTHER INFORMATION: Synthetic peptide

<400> SEQUENCE: 6

Cys Leu Ser Pro Glu Glu Pro Ala Pro Glu Ser Pro Gln Val Pro Glu
1               5                   10                  15

Ala Pro Gly Gly Ser Ala Val
            20

<210> SEQ ID NO 7
<211> LENGTH: 26
<212> TYPE: PRT
<213> ORGANISM: Artificial Sequence
<220> FEATURE:
<223> OTHER INFORMATION: Synthetic peptide

<400> SEQUENCE: 7

Cys Ser Leu Pro Glu Glu Pro Ala Pro Glu Ala Pro Glu Thr Pro Glu
1               5                   10                  15

Thr Pro Glu Ala Pro Gly Gly Ser Ala Val
            20                  25
```